US011135345B2

(12) United States Patent
Kalaskar et al.

(10) Patent No.: US 11,135,345 B2
(45) Date of Patent: Oct. 5, 2021

(54) ON DEMAND DIALYSATE MIXING USING CONCENTRATES

(71) Applicant: Fresenius Medical Care Holdings, Inc., Waltham, MA (US)

(72) Inventors: Shashikant Dattatraya Kalaskar, Ogden, UT (US); Justin Clark, Farmington, UT (US); Tao Jiang, Kaysville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 728 days.

(21) Appl. No.: 15/591,196

(22) Filed: May 10, 2017

(65) Prior Publication Data

US 2018/0326138 A1 Nov. 15, 2018

(51) Int. Cl.
*A61M 1/16* (2006.01)
*A61M 1/28* (2006.01)
(Continued)

(52) U.S. Cl.
CPC ............. *A61M 1/1666* (2014.02); *A61K 9/20* (2013.01); *A61K 31/194* (2013.01);
(Continued)

(58) Field of Classification Search
CPC ...... A61M 1/1666; A61M 1/1656; A61K 9/20
See application file for complete search history.

(56) References Cited

U.S. PATENT DOCUMENTS 1,406,372 A 2/1922 Grapp
1,689,432 A 10/1928 Hartwig
(Continued)

FOREIGN PATENT DOCUMENTS

DE 10204003 8/2003
EP 0034916 9/1981
(Continued)

OTHER PUBLICATIONS

Communication from European Patent Office from European Application No. 13/780,435.7, dated Feb. 1, 2016, 8 pages.
(Continued)

*Primary Examiner* — Tatyana Zalukaeva
*Assistant Examiner* — Jessica R Arble
(74) *Attorney, Agent, or Firm* — Leydig, Voit & Mayer, Ltd.

(57) ABSTRACT

A dialysate mixing machine may be configured to make dialysate on demand using, among other things, a plurality of concentrates in solid tablet form. For example, a prescription may be received by the dialysate mixing machine indicating the particular chemical constituents and amounts of each chemical constituent to be included in the dialysate. Based on the prescription, the dialysate mixing machine can determine the number of tablets required for each chemical constituent (and, e.g., the required amounts of other chemical constituents that are not in tablet form). The tablets are automatically dispensed and mixed with purified water, bicarbonate, and sodium chloride in a mixing chamber to produce the dialysate according to the prescription. The dialysate mixing machine may be used with and/or coupled to a dialysis machine (e.g., a hemodialysis (HD) machine designed for home use) to provide the dialysate on demand for a dialysis treatment.

25 Claims, 6 Drawing Sheets

(51) Int. Cl.
  *A61M 1/36* (2006.01)
  *A61K 9/20* (2006.01)
  *A61K 33/14* (2006.01)
  *A61K 31/194* (2006.01)
  *A61K 31/7004* (2006.01)

(52) U.S. Cl.
  CPC .......... *A61K 31/7004* (2013.01); *A61K 33/14* (2013.01); *A61M 1/1656* (2013.01); *A61M 1/287* (2013.01); *A61M 1/3627* (2013.01); *A61M 2205/3306* (2013.01); *A61M 2205/3317* (2013.01); *A61M 2205/3368* (2013.01); *A61M 2205/3553* (2013.01); *A61M 2205/3584* (2013.01); *A61M 2205/36* (2013.01); *A61M 2205/50* (2013.01); *A61M 2205/505* (2013.01); *A61M 2205/52* (2013.01); *A61M 2205/6072* (2013.01)

(56) References Cited

U.S. PATENT DOCUMENTS

| | | | |
|---|---|---|---|
| 2,107,173 | A | 2/1938 | Bauer |
| 2,982,895 | A | 5/1961 | Exon |
| 3,130,289 | A | 4/1964 | Katzman et al. |
| 3,605,783 | A | 9/1971 | Pecker et al. |
| 3,694,625 | A | 9/1972 | Cole |
| 3,738,356 | A | 6/1973 | Workman |
| 3,762,557 | A | 10/1973 | Tudor et al. |
| 3,808,401 | A | 4/1974 | Wright et al. |
| 3,987,385 | A | 10/1976 | Diller et al. |
| 4,014,319 | A | 3/1977 | Favre |
| 4,136,708 | A | 1/1979 | Cosentino et al. |
| 4,315,523 | A | 2/1982 | Mahawili et al. |
| 4,399,036 | A * | 8/1983 | Babb ................. A61M 1/1656 210/638 |
| 4,489,535 | A | 12/1984 | Veltman |
| 4,503,706 | A | 3/1985 | Kolodjski |
| 4,508,622 | A | 4/1985 | Polaschegg et al. |
| 4,613,325 | A | 9/1986 | Abrams |
| 4,618,343 | A | 10/1986 | Polaschegg |
| 4,676,467 | A | 6/1987 | Palsulich |
| 4,718,447 | A | 1/1988 | Marshall |
| 4,734,198 | A | 3/1988 | Harm et al. |
| 4,753,370 | A | 6/1988 | Rudick |
| 4,756,330 | A | 7/1988 | Tischer |
| 4,756,331 | A | 7/1988 | Stegmaier |
| 4,778,451 | A | 10/1988 | Kamen |
| 4,808,161 | A | 2/1989 | Kamen |
| 4,812,239 | A | 3/1989 | Mills |
| 4,826,482 | A | 5/1989 | Kamen |
| 4,869,286 | A | 9/1989 | Williams et al. |
| 4,895,657 | A | 1/1990 | Polaschegg |
| 4,902,282 | A | 2/1990 | Bellotti et al. |
| 4,902,877 | A | 2/1990 | Grasso et al. |
| 4,941,353 | A | 7/1990 | Fukatsu et al. |
| 4,950,134 | A | 8/1990 | Bailey et al. |
| 4,967,932 | A | 11/1990 | Wiley et al. |
| 4,976,162 | A | 12/1990 | Kamen |
| 4,979,639 | A | 12/1990 | Hoover et al. |
| 5,002,471 | A | 3/1991 | Perlov |
| 5,015,389 | A | 5/1991 | Portillo et al. |
| 5,024,756 | A | 6/1991 | Sternby |
| 5,058,630 | A | 10/1991 | Wiley et al. |
| 5,074,359 | A | 12/1991 | Schmidt |
| 5,088,515 | A | 2/1992 | Kamen |
| 5,100,554 | A | 3/1992 | Polaschegg |
| 5,116,021 | A | 5/1992 | Faust et al. |
| 5,121,855 | A | 6/1992 | Credle, Jr. |
| 5,141,130 | A | 8/1992 | Wiley et al. |
| 5,141,493 | A | 8/1992 | Jacobsen et al. |
| 5,146,713 | A | 9/1992 | Grafius |
| 5,178,182 | A | 1/1993 | Kamen |
| 5,181,631 | A | 1/1993 | Credle, Jr. |
| 5,192,000 | A | 3/1993 | Wandrick et al. |
| 5,193,990 | A | 3/1993 | Kamen et al. |
| 5,211,201 | A | 5/1993 | Kamen et al. |
| 5,241,985 | A | 9/1993 | Faust et al. |
| 5,252,213 | A * | 10/1993 | Ahmad ................. A61M 1/169 210/542 |
| 5,300,301 | A * | 4/1994 | Lakin ..................... A61K 31/19 424/464 |
| 5,311,899 | A | 5/1994 | Isayama et al. |
| 5,324,422 | A | 6/1994 | Collerun et al. |
| 5,344,392 | A | 9/1994 | Senninger et al. |
| 5,350,082 | A | 9/1994 | Kiriakides et al. |
| 5,350,357 | A | 9/1994 | Kamen et al. |
| D351,470 | S | 10/1994 | Scherer et al. |
| 5,353,837 | A | 10/1994 | Faust |
| 5,395,351 | A | 3/1995 | Munsch |
| 5,421,208 | A | 6/1995 | Packard et al. |
| 5,421,823 | A | 6/1995 | Kamen et al. |
| 5,431,626 | A | 7/1995 | Bryant et al. |
| 5,437,842 | A | 8/1995 | Jensen et al. |
| 5,438,510 | A | 8/1995 | Bryant et al. |
| 5,447,286 | A | 9/1995 | Kamen et al. |
| 5,474,683 | A | 12/1995 | Bryant et al. |
| 5,486,286 | A | 1/1996 | Peterson et al. |
| 5,490,447 | A | 2/1996 | Giulaino |
| 5,499,741 | A | 3/1996 | Scott et al. |
| 5,540,265 | A | 7/1996 | Polaschegg et al. |
| 5,570,716 | A | 11/1996 | Kamen et al. |
| 5,572,992 | A | 11/1996 | Kankkunen et al. |
| 5,583,948 | A | 12/1996 | Shibayama |
| 5,616,248 | A | 4/1997 | Schal |
| 5,628,908 | A | 5/1997 | Kamen et al. |
| 5,634,896 | A | 6/1997 | Bryant et al. |
| 5,640,995 | A | 6/1997 | Packard et al. |
| 5,641,405 | A | 6/1997 | Keshaviah et al. |
| 5,641,892 | A | 6/1997 | Larkins et al. |
| 5,642,761 | A | 7/1997 | Holbrook |
| 5,713,865 | A | 2/1998 | Manning et al. |
| 5,728,949 | A | 3/1998 | McMillan et al. |
| 5,741,125 | A | 4/1998 | Neftel et al. |
| 5,755,683 | A | 5/1998 | Houle et al. |
| 5,757,667 | A | 5/1998 | Shannon et al. |
| 5,771,914 | A | 6/1998 | Ling et al. |
| 5,772,637 | A | 6/1998 | Heinzmann et al. |
| 5,788,099 | A | 8/1998 | Treu et al. |
| 5,797,519 | A | 8/1998 | Schroeder et al. |
| 5,803,320 | A | 9/1998 | Cutting et al. |
| 5,811,581 | A | 9/1998 | Piva |
| 5,884,813 | A | 3/1999 | Bordonaro et al. |
| 5,887,621 | A | 3/1999 | Doll |
| 5,925,011 | A | 7/1999 | Faict et al. |
| 5,925,014 | A | 7/1999 | Teeple, Jr. |
| 5,938,634 | A | 8/1999 | Packard |
| 5,939,644 | A | 8/1999 | Hsu |
| 5,960,997 | A | 10/1999 | Forsythe |
| 5,967,367 | A | 10/1999 | Orsborn |
| 5,989,423 | A | 11/1999 | Kamen |
| 5,992,685 | A | 11/1999 | Credle, Jr. |
| 5,997,502 | A | 12/1999 | Reilly et al. |
| 6,026,847 | A | 2/2000 | Reinicke et al. |
| 6,036,680 | A | 3/2000 | Horne et al. |
| 6,041,801 | A | 3/2000 | Gray et al. |
| 6,042,784 | A | 3/2000 | Wamsiedler et al. |
| 6,065,941 | A | 5/2000 | Gray et al. |
| 6,067,946 | A | 5/2000 | Bunker et al. |
| 6,070,761 | A | 6/2000 | Bloom et al. |
| 6,118,207 | A | 9/2000 | Ormerud et al. |
| 6,126,831 | A | 10/2000 | Goldau et al. |
| 6,164,621 | A | 12/2000 | Bouchard et al. |
| 6,165,154 | A | 12/2000 | Gray et al. |
| 6,187,199 | B1 | 2/2001 | Goldau |
| 6,210,361 | B1 | 4/2001 | Kamen et al. |
| 6,220,295 | B1 | 4/2001 | Bouchard et al. |
| 6,223,130 | B1 | 4/2001 | Gray et al. |
| 6,234,997 | B1 | 5/2001 | Kamen et al. |
| 6,251,437 | B1 * | 6/2001 | Fischbach ................. A61K 9/08 424/489 |
| 6,274,106 | B1 | 8/2001 | Held |
| 6,312,589 | B1 | 11/2001 | Jarocki et al. |
| 6,316,864 | B1 | 11/2001 | Ormerod |

(56) References Cited

U.S. PATENT DOCUMENTS

| | | |
|---|---|---|
| 6,321,587 B1 | 11/2001 | Demers et al. |
| 6,343,614 B1 | 2/2002 | Gray et al. |
| 6,364,159 B1 | 4/2002 | Newman et al. |
| 6,364,857 B1 | 4/2002 | Gray et al. |
| 6,382,923 B1 | 5/2002 | Gray |
| 6,406,276 B1 | 6/2002 | Normand et al. |
| 6,416,293 B1 | 7/2002 | Bouchard et al. |
| 6,451,211 B1 | 9/2002 | Plester et al. |
| 6,459,175 B1 | 10/2002 | Potega |
| 6,464,667 B1 | 10/2002 | Kamen et al. |
| 6,468,424 B1 | 10/2002 | Dönig et al. |
| 6,497,676 B1 | 12/2002 | Childers et al. |
| 6,503,062 B1 | 1/2003 | Gray et al. |
| 6,520,747 B2 | 2/2003 | Gray et al. |
| 6,550,642 B2 | 4/2003 | Newman et al. |
| 6,558,343 B1 | 5/2003 | Neftel |
| 6,564,971 B2 | 5/2003 | Heyes |
| 6,592,542 B2 | 7/2003 | Childers et al. |
| 6,595,944 B2 | 7/2003 | Balschat et al. |
| 6,600,882 B1 | 7/2003 | Applegate et al. |
| 6,604,908 B1 | 8/2003 | Bryant et al. |
| 6,613,280 B2 | 9/2003 | Myrick et al. |
| 6,614,008 B2 | 9/2003 | Tidrick |
| 6,625,824 B1 | 9/2003 | Lutz et al. |
| 6,640,650 B2 | 11/2003 | Matsuzawa et al. |
| 6,648,240 B2 | 11/2003 | Simmons |
| 6,648,845 B1 | 11/2003 | Gotch et al. |
| 6,663,359 B2 | 12/2003 | Gray |
| 6,669,051 B1 | 12/2003 | Phallen et al. |
| 6,669,053 B1 | 12/2003 | Garson et al. |
| 6,685,831 B2 | 2/2004 | Dönig et al. |
| 6,702,774 B1 | 3/2004 | Polaschegg |
| 6,709,417 B1 | 3/2004 | Houle et al. |
| 6,726,656 B2 | 4/2004 | Kamen et al. |
| 6,729,226 B2 | 5/2004 | Mangiapane |
| 6,745,592 B1 | 6/2004 | Edgington et al. |
| 6,746,514 B2 | 6/2004 | Bedingfield et al. |
| 6,749,403 B2 | 6/2004 | Bryant et al. |
| 6,756,069 B2 | 6/2004 | Scoville et al. |
| 6,764,761 B2 | 7/2004 | Eu et al. |
| 6,792,847 B2 | 9/2004 | Tobin et al. |
| 6,807,460 B2 | 10/2004 | Black et al. |
| 6,808,369 B2 | 10/2004 | Gray et al. |
| 6,814,547 B2 | 11/2004 | Childers et al. |
| 6,845,886 B2 | 1/2005 | Henry et al. |
| 6,860,866 B1 | 3/2005 | Graf et al. |
| 6,869,538 B2 | 3/2005 | Yu et al. |
| 6,911,007 B2 | 6/2005 | Nier et al. |
| 6,925,011 B2 | 8/2005 | Pekny et al. |
| 7,084,769 B2 | 8/2006 | Bauer et al. |
| 7,108,790 B2 | 9/2006 | Collins et al. |
| 7,214,210 B2 | 5/2007 | Kamen |
| 7,223,426 B2 | 5/2007 | Cheng et al. |
| 7,232,059 B2 | 6/2007 | Peebles |
| D556,909 S | 12/2007 | Reihanifam et al. |
| D556,910 S | 12/2007 | Reihanifam et al. |
| D576,281 S | 9/2008 | Reihanifam et al. |
| 7,617,850 B1 | 11/2009 | Dorney |
| 7,740,152 B2 | 5/2010 | Hughes et al. |
| 7,878,370 B2 | 2/2011 | Sevcik et al. |
| 8,087,303 B2 | 1/2012 | Beavis |
| 8,516,902 B2 | 8/2013 | Beavis et al. |
| 8,870,811 B2 | 10/2014 | Gavin et al. |
| 9,517,296 B2 | 12/2016 | Fulkerson et al. |
| 9,675,743 B2 | 6/2017 | Raiford et al. |
| 2002/0000793 A1 | 1/2002 | Hanaki |
| 2002/0008032 A1 | 1/2002 | Hayenga |
| 2002/0029804 A1 | 3/2002 | Liorati et al. |
| 2002/0060226 A1 | 5/2002 | Kameyama |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0029451 A1 | 2/2003 | Blair et al. |
| 2003/0085621 A1 | 5/2003 | Potega |
| 2003/0111457 A1 | 6/2003 | Tidrick |
| 2003/0130606 A1 | 7/2003 | Tuck |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman, Jr. et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0122353 A1 | 6/2004 | Shahmirian et al. |
| 2004/0135078 A1 | 7/2004 | Mandro et al. |
| 2004/0195190 A1 | 10/2004 | Min et al. |
| 2004/0261624 A1 | 12/2004 | Lassota |
| 2005/0103799 A1 | 5/2005 | Litterst et al. |
| 2005/0113734 A1 | 5/2005 | Brugger et al. |
| 2005/0151422 A1 | 7/2005 | Gilmour |
| 2005/0201200 A1 | 9/2005 | Fleig |
| 2005/0230292 A1 | 10/2005 | Beden et al. |
| 2005/0234381 A1 | 10/2005 | Niemetzer et al. |
| 2005/0242034 A1 | 11/2005 | Connell et al. |
| 2006/0027267 A1 | 2/2006 | Fritze |
| 2006/0044192 A1 | 3/2006 | Egbert |
| 2006/0081653 A1 | 4/2006 | Boland et al. |
| 2006/0195064 A1 | 8/2006 | Plahey et al. |
| 2006/0241550 A1 | 10/2006 | Kamen |
| 2007/0085049 A1 | 4/2007 | Houle |
| 2007/0152829 A1 | 7/2007 | Lindsay et al. |
| 2008/0008609 A1 | 1/2008 | Pate et al. |
| 2008/0054837 A1 | 3/2008 | Beavis et al. |
| 2008/0073610 A1 | 3/2008 | Manning |
| 2008/0204347 A1 | 8/2008 | Alvey et al. |
| 2009/0159612 A1 | 6/2009 | Beavis |
| 2012/0138533 A1 | 6/2012 | Curtis et al. |
| 2012/0203573 A1* | 8/2012 | Mayer .................. G06F 19/3456 705/3 |
| 2014/0276376 A1 | 9/2014 | Rohde et al. |
| 2015/0168188 A1 | 6/2015 | Reichart |
| 2016/0101225 A1* | 4/2016 | Smith .................. A61M 1/1696 210/662 |
| 2016/0109398 A1 | 4/2016 | Fulkerson et al. |
| 2016/0239674 A1 | 8/2016 | Miller et al. |
| 2017/0043089 A1* | 2/2017 | Handler ................ G16H 20/17 |
| 2017/0050834 A1 | 2/2017 | Beavis et al. |
| 2017/0176558 A1 | 6/2017 | Jones et al. |
| 2017/0281846 A1* | 10/2017 | Manda .................. A61M 1/282 |
| 2017/0326282 A1* | 11/2017 | Wilt .................... A61M 1/1656 |
| 2018/0043080 A1 | 2/2018 | Gerber et al. |

FOREIGN PATENT DOCUMENTS

| | | |
|---|---|---|
| EP | 0311848 | 4/1989 |
| EP | 0399918 | 11/1990 |
| EP | 0532062 | 11/1995 |
| EP | 0875431 | 11/1998 |
| EP | 0796218 | 7/1999 |
| EP | 1050753 | 11/2000 |
| EP | 1187642 | 3/2002 |
| EP | 1277485 | 11/2006 |
| EP | 1783568 | 5/2007 |
| FR | 2569560 | 3/1986 |
| FR | 2769954 | 4/1999 |
| GB | 2091126 | 7/1982 |
| JP | 20040093065 | 3/2004 |
| WO | 9211046 | 7/1992 |
| WO | 9218048 | 10/1992 |
| WO | 9511855 | 5/1995 |
| WO | 9625214 | 8/1996 |

(56) References Cited

FOREIGN PATENT DOCUMENTS

| WO | 9700400 | 1/1997 | | |
|---|---|---|---|---|
| WO | 9937342 | 7/1999 | | |
| WO | 0057935 | 10/2000 | | |
| WO | WO-0057935 A1 * | 10/2000 | .......... | A61M 1/1686 |
| WO | 0183360 | 11/2001 | | |
| WO | 2002049968 | 6/2002 | | |
| WO | 02059035 | 8/2002 | | |
| WO | 2004089441 | 10/2004 | | |
| WO | 2006036353 | 4/2006 | | |
| WO | 20080143289 | 11/2008 | | |
| WO | 2009090354 | 7/2009 | | |
| WO | 2011066299 | 6/2011 | | |
| WO | 2012041790 | 4/2012 | | |
| WO | 2016049542 | 3/2016 | | |

OTHER PUBLICATIONS

DePaula et al., "Clinical consequences of an individualized dialysate sodium prescription in hemodialysis patients," Kidney International, 2004, 66:1232-1238.

European Search Report dated Mar. 15, 2013, received in European Patent Application No. 08829307.1, 4 pages.

Gambro®, "DEHP-free cartridge blood sets," © Nov. 2004, Gambro Inc., Lakewood, CO, 4 pages.

Gambro®, "Prismaflex™ anticipating critical care needs and taking our innovative response . . . to new heights," © 2004, Gambro Inc., Lakewood, CO, 8 pages.

Gotch et al., "Mechanisms determining the ration of conductivity clearance to urea clearance," Kidney International, 2004, 66(89):S1-S22, 24 pages.

International Preliminary Report and Written Opinion, dated Mar. 18, 2010, received in International Application No. PCT/US08/075502, 7 pages.

International Preliminary Report on Patentability and Written Opinion dated Sep. 7, 2012, received in International Patent Application No. PCT/US2011/026274, 9 pages.

International Preliminary Report on Patentability and Written Opinion, dated Mar. 18, 2010, received in International Application No. PCT/US08/75480, 9 pages.

International Preliminary Report on Patentability dated Mar. 29, 2012, received in International Patent Application No. PCT/US2009/055388, 7 pages.

International Preliminary Report on Patentability, dated Mar. 18, 2010, received in International Application No. PCT/US2008/075473, 6 pages.

International Preliminary Report on Patentability, dated Mar. 18, 2010, received in International Application No. PCT/US/08/075497, 8 pages.

International Search Report and Written Opinion dated Mar. 5, 2013, received in International Patent Application No. PCT/US2012/062215, 12 pages.

International Search Report and Written Opinion dated Mar. 6, 2012, received in International Application No. PCT/US2009/0055388, 12 pages.

International Search Report and Written Opinion, dated Dec. 5, 2008, received in International Application No. PCT/US08/075480, 11 pages.

International Search Report and Written Opinion, dated Dec. 29, 2008, received in International Application No. PCT/US08/075497, 10 pages.

International Search Report and Written Opinion, dated Mar. 6, 2009, received in International Application No. PCT/US08/075473, 9 pages.

International Search Report and Written Opinion, dated Mar. 18, 2010, received in International Application No. PCT/US08/075502, 7 pages.

International Search Report and Written Opinion, dated Sep. 7, 2011, received in International Application No. PCT/US2010/033977, 12 pages.

Liljencranis, Johan, Thermal Anemometers Amateur Design Report, Jul. 17, 2004. URL<http://fonema.se/anemom/anemom.html>.

Sleep Safe™ Operating Instructions, Fresenius Medical Care, Aug. 2000, 134 pages.

U.S. Appl. No. 29/224,370, filed Feb. 28, 2005, and entitled "Peritoneal Dialysis Cycler".

U.S. Appl. No. 29/224,371, filed Feb. 28, 2005, and entitled "Cassette for Peritoneal Dialysis Cycler".

U.S. Appl. No. 29/224,375, filed Feb. 28, 2005, and entitled "Peritoneal Dialysis Cycler".

Zhou et al., "Impact of sodium and ultrafiltration profiling on haemodialysis-related hypotension," NDT Advance Access published online on Sep. 5, 2006.

International Preliminary Report on Patentability in Application No. PCT/US2018/029061, dated Nov. 12, 2019, 9 pages.

International Search Report and Written Opinion in International Application No. PCT/US2018/029061, dated Jul. 17, 2018, 16 pages.

International Patent Application No. PCT/US2020/021465, Search Report (dated May 19, 2020).

* cited by examiner

ON DEMAND DIALYSATE MIXING USING CONCENTRATES

TECHNICAL FIELD

This invention relates to on demand dialysate mixing using concentrates.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis (HD)—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then typically discarded.

The dialysis solutions or dialysates used during hemodialysis typically contain sodium chloride and other electrolytes, such as calcium chloride or potassium chloride, a buffer substance, such as bicarbonate or acetate, and acid to establish a physiological pH, plus, optionally, glucose or another osmotic agent.

Another type of dialysis treatment is peritoneal dialysis (PD) that utilizes the patient's own peritoneum, a membranous lining of the abdominal body cavity. With its good perfusion properties, the peritoneum is capable of acting as a natural semi-permeable membrane for transferring water and waste products to a type of dialysate solution known as PD solution introduced temporarily into the patient's abdominal cavity. An access port is implanted in the patient's abdomen and the PD solution is infused usually by a pump into the patient's abdomen through a patient line and left to dwell for a period of time and then drained out. This procedure is usually repeated multiple times for a complete treatment. PD machines, such as Automated PD (APD) machines or PD cyclers, are designed to facilitate or control the PD process so that it can be performed at home without clinical staff in attendance.

SUMMARY

In one aspect, a dialysate mixing machine includes a dialysate mixing chamber, a dispenser configured to provide chemical concentrates to the dialysate mixing chamber, and a control unit configured to process a dialysate prescription to cause the dispenser to provide chemical concentrates in amounts based on the dialysate prescription. The chemical concentrates are combined with at least water in the dialysate mixing chamber to form a dialysate according to the dialysate prescription.

Implementations can include one or more of the following features.

In some implementations, the chemical concentrates are in solid tablet form.

In some implementations, a size and shape of the solid tablets for each chemical concentrate is different than a size and shape of the solid tablets for each other chemical concentrate.

In some implementations, the dialysate prescription indicates a number of solid tablets to be dispensed for each chemical concentrate.

In some implementations, each chemical concentrate is stored in the dispenser as a stack of solid tablets.

In some implementations, each stack of solid tablets is held in a housing that includes a machine-readable indicium. The machine-readable indicium includes information related to the chemical concentrate held in the housing.

In some implementations, the machine-readable indicium is a barcode.

In some implementations, the barcode includes information related to a type of the chemical concentrate and an amount of the chemical concentrate in each tablet.

In some implementations, the chemical concentrates include one or more of potassium chloride, calcium chloride, magnesium chloride, citric acid, and dextrose.

In some implementations, the dialysate prescription indicates that the dialysate is to have a proportioning ratio of 45X.

In some implementations, a bicarbonate solution is also combined in the dialysate mixing chamber to form the dialysate.

In some implementations, a sodium chloride solution is also combined in the dialysate mixing chamber to form the dialysate.

In some implementations, the dialysate mixing machine also includes one or more conductivity sensors configured to obtain conductivity measurements of the bicarbonate solution and the sodium chloride solution. The conductivity measurements are used to confirm that a concentration of the bicarbonate solution and a concentration of the sodium chloride solution conform to the dialysate prescription.

In some implementations, the chemical concentrates are in liquid form.

In some implementations, the dialysate mixing machine also includes a receiving unit configured to receive the dialysate prescription.

In some implementations, the receiving unit receives the dialysate prescription wirelessly.

In another aspect, a dialysis system includes a dialysis machine and a dialysate mixing machine coupled to the dialysis machine. The dialysate mixing machine includes a dialysate mixing chamber, a dispenser configured to provide chemical concentrates to the dialysate mixing chamber, and a control unit configured to process a dialysate prescription to cause the dispenser to provide chemical concentrates in amounts based on the dialysate prescription. The chemical concentrates are combined with at least water in the dialysate mixing chamber to form a dialysate according to the dialysate prescription.

Implementations can include one or more of the following features.

In some implementations, the dialysis machine is a peritoneal dialysis machine.

In some implementations, the dialysis machine is a hemodialysis machine that includes a blood pump configured to pump blood to and from a patient, and a dialyzer configured to receive the blood from the patient and the dialysate from the dialysate mixing chamber, remove toxins from the blood, and provide filtered blood to the patient.

In some implementations, the blood and the dialysate flow through the dialyzer at a flow fraction of less than 0.5.

In some implementations, 45 liters or less of dialysate are made in the dialysate mixing chamber, and the hemodialysis machine provides a hemodialysis treatment to the patient using the 45 liters or less of dialysate.

In some implementations, a weekly treatment adequacy of at least 2 Kt/V is achieved by providing six or fewer hemodialysis treatments to the patient per week. Each hemodialysis treatment has a duration of between three and six hours.

In another aspect, a method includes receiving, by an HD machine, a dialysate prescription, and causing a dispenser of the HD machine to provide chemical concentrates to a dialysate mixing chamber in amounts based on the dialysate prescription. The chemical concentrates are combined with at least water in the dialysate mixing chamber to form a dialysate according to the dialysate prescription.

In some implementations, the chemical concentrates are in solid tablet form.

In some implementations, the dialysate prescription indicates a number of solid tablets to be dispensed for each chemical concentrate.

In some implementations, each chemical concentrate is stored in the dispenser as a stack of solid tablets.

In some implementations, each stack of solid tablets is held in a housing that includes a machine-readable indicium. The machine-readable indicium includes information related to the chemical concentrate held in the housing.

In some implementations, the chemical concentrates are in liquid form.

Implementations can include one or more of the following advantages.

In some implementations, the systems and methods described herein can allow dialysate to be prepared according to a dialysate prescription for a particular patient and/or a particular treatment on demand, thereby reducing or eliminating the need to store dialysate and/or liquid concentrates for extended periods of time. Pre-made dialysate and existing concentrates require large storage space and delivery containers (e.g., drums) with known problems and high maintenance costs.

In some implementations, including each chemical concentrate in its own pre-weighted solid tablet form allows the dialysate to be created while relying on minimal different product codes for the various chemical concentrate. For example, to prepare a predetermined volume of dialysate according to the prescription, the particular amount of each chemical concentrate can be determined and individually added to the dialysate mixing chamber without relying on existing concentrates of various forms and having various combinations of chemicals. Such a simplified process can eliminate the need for acid-base proportioning capability in the dialysis machine.

In some implementations, the process of creating the dialysate (e.g., for home hemodialysis use) can be simplified for the patient. For example, after the patient has been verified, the dialysate can be prepared according to an existing prescription while requiring minimal interaction on the part of the patient. In some implementations, the dialysis machine can maintain a history of the various dialysate prescriptions used to create dialysate in the past. In some implementations, the dialysis machine can remember the last dialysate prescription that was prepared for a particular patient, and provide a recommendation to the patient to create dialysate according to the same dialysate prescription. In this way, if the patient's prescription has not changed, the patient can cause the dialysis machine to make the dialysate by simply confirming the dialysis machine's suggestion (e.g., with a single press of a button).

The details of one or more embodiments of the invention are set forth in the accompanying drawings and the description below. Other aspects, features, and advantages will be apparent from the description and drawings, and from the claims.

DETAILED DESCRIPTION

A dialysate mixing machine may be configured to make dialysate on demand using, among other things, a plurality of concentrates in solid tablet form. For example, a prescription may be received by the dialysate mixing machine indicating the particular chemical constituents and amounts of each chemical constituent to be included in the dialysate. Based on the prescription, the dialysate mixing machine can determine the number of tablets required for each chemical constituent and the required amounts of other chemical constituents that are not in concentrated form. The tablets are automatically dispensed and mixed with purified water, bicarbonate, and sodium chloride in a mixing chamber to produce the dialysate according to the prescription. Such a technique allows for the chemical constituents to be delivered and stored in a tablet form that requires minimal storage space and oversight. The mixing technique requires less storage space than is otherwise typically required for mixing and storing dialysate using existing techniques because the dialysate can be made only in an amount that is necessary for an impending treatment session. Further, because the chemical constituents are added in the amounts required to make the final dialysate according to the prescription, the dialysate mixing machine can prepare the dialysate without requiring an acid-base proportioning system.

In some implementations, a flow fraction (e.g., a ratio of dialysate flow rate ($Q_d$) to blood flow rate ($Q_b$)) can be reduced such that a relatively small volume (e.g., 45 liters or less) of dialysate is required to achieve an acceptable treatment adequacy (e.g., a weekly treatment adequacy of at least 2 Kt/V) for the patient. For example, in some implementations, a flow fraction of less than 0.5 can be employed, in which $Q_d$ is approximately 120 ml/min and $Q_b$ is approximately 300 ml/min, and in which six hemodialysis treatments of approximately three hours each can be provided per week, thereby resulting in a weekly treatment adequacy of at least 2 Kt/V for an average male patient. Such a treatment schedule would require approximately 22 liters of dialysate per treatment. Such a volume of dialysate can be easily generated by the hemodialysis machine with minimal patient interaction using the techniques described herein.

Figure 1:
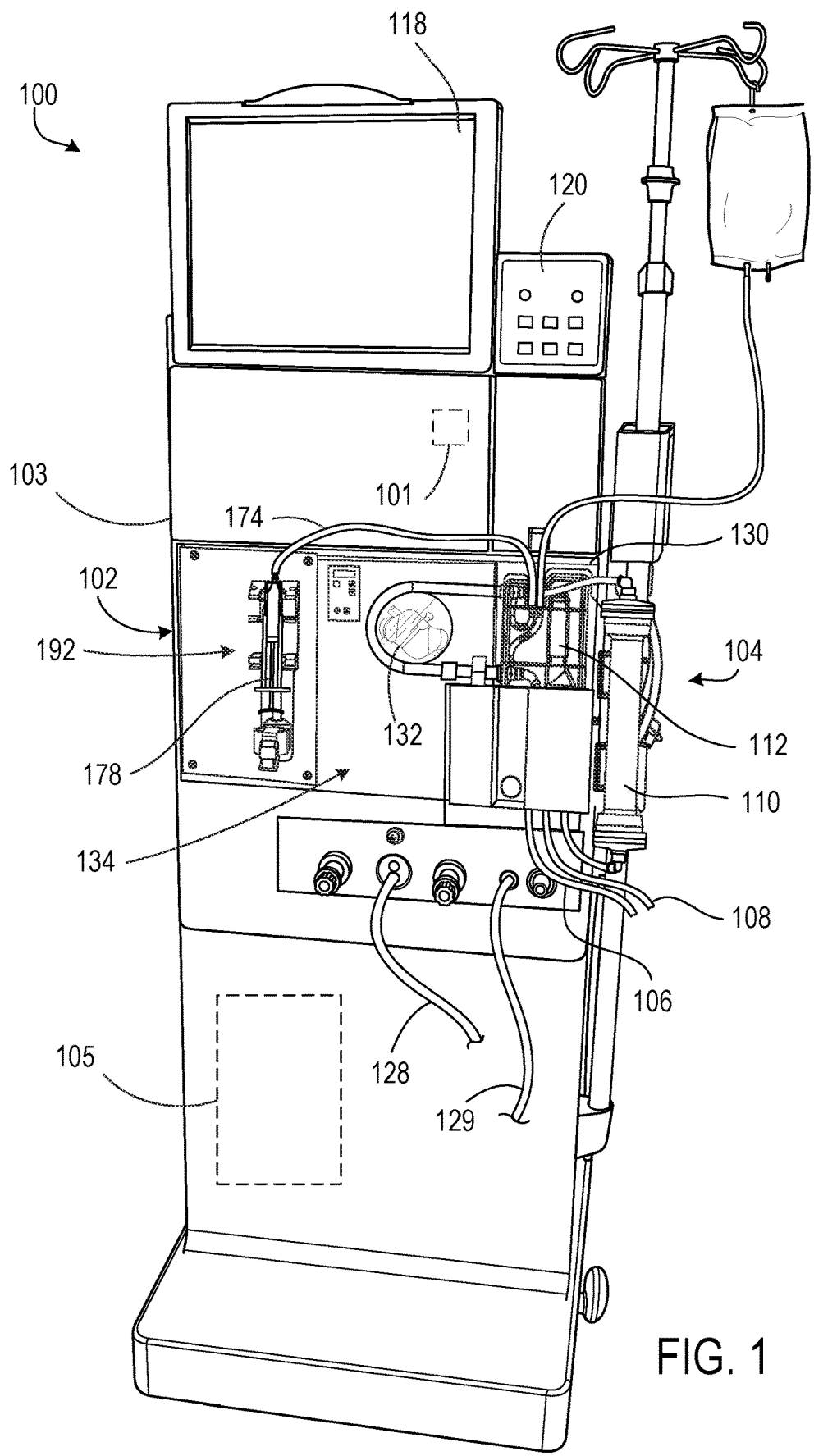
FIG. 1 is a front perspective view of a hemodialysis system that includes a dialysate mixing system.

FIG. 1 shows a dialysis system, in particular, a hemodialysis system 100. Although the system described herein is largely discussed in connection with hemodialysis systems by way of example, it is explicitly noted that the system described herein may be used in connection with other types of medical devices and treatments, including peritoneal dialysis (PD) systems. The hemodialysis system 100 includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 includes an air release device 112. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment that is sized and shaped to receive the blood component set 104. In the closed position, the door presses certain blood components of the blood component set 104 against corresponding instruments exposed on the front face of the module 130.

The blood pump 132 is part of a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

The dialysate is created by the hemodialysis machine 102 "on demand". That is, the hemodialysis machine 102 is configured to mix various constituents of the dialysate together to form a dialysate having requisite characteristics. The dialysate can be created for a particular patient and/or for a particular dialysis treatment session (e.g., according to a dialysate prescription), as described in more detail below. In this way, dialysate having the necessary characteristics can be created when it is needed, thereby reducing or eliminating the difficulty involved in storing dialysate for extended periods of time.

The hemodialysis machine 102 includes a dialysate mixing system 105 for mixing dialysate. In some implementations, the dialysate mixing system 105 is referred to as a dialysate mixing machine. In particular, as described in more detail below with respect to FIG. 2, the dialysate mixing system 105 includes a dialysate mixing chamber (220 of FIG. 2) that is internal to the housing 103 of the hemodialysis machine 102. Water, sodium chloride (NaCl), bicarbonate (NaHCO$_3$), and a plurality of chemical concentrates are mixed together in the dialysate mixing chamber 220 to form the dialysate. The dialysate mixing chamber 220 is connected to the dialyzer 110 via at least a dialysate supply line, which is also internal to the housing 103 of the hemodialysis machine 102. A drain line 128 and an ultrafiltration line 129 extend from the hemodialysis machine 102. The drain line 128 and the ultrafiltration line 129 are fluidly connected to the various dialysate components and dialysate lines inside the housing 103 of the hemodialysis machine 102 that form part of the dialysate circuit. During hemodialysis, the dialysate supply line carries fresh dialysate from the dialysate mixing chamber 220 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100.

The hemodialysis machine 102 also includes a control unit 101 (e.g., a processor) configured to receive signals from and transmit signals to the touch screen 118 and the control panel 120. The control unit 101 can control the operating parameters of the hemodialysis machine 102, for example, based at least in part on the signals received by the touch screen 118 and the control panel 120.

The control unit 101 is also configured to process prescriptions (e.g., a dialysate prescription) and cause the hemodialysis machine 102 to create a dialysate according to the dialysate prescription. For example, the dialysate prescription may be received by a receiving unit of the hemodialysis machine 102 (e.g., from a medical database over a secured network) or otherwise provided to the hemodialysis machine 102. In some implementations, the dialysate prescription is wirelessly received by the receiving unit. The dialysate prescription may include information indicating the particular chemical constituents and amounts of each chemical constituent to be included in the dialysate. The control unit 101 can process the dialysate prescription and provide control signals to the hemodialysis machine 102 to cause the hemodialysis machine 102 to create the dialysate. In particular, the control unit 101 can cause particular amounts of each chemical concentrate to be added to the dialysate mixing chamber 220 to be combined with water, sodium chloride, and bicarbonate to form the dialysate.

In some implementations, the term "prescription" may be understood to indicate a treatment that a medical professional prescribes to the patient and may be captured as prescription parameters in the patient's electronic health record (EHR). The prescription (e.g., the prescription parameters) may be appropriately translated, formatted, encrypted, and/or otherwise converted into a digital prescription file that contains the program and/or instruction sets for the medical device (e.g., a dialysate mixing machine, a dialysis machine, etc.) to carry out the prescribed treatment. The term "prescription" used herein may be generally understood to refer the treatment, parameters, and/or prescription file, as appropriate.

Figure 2:
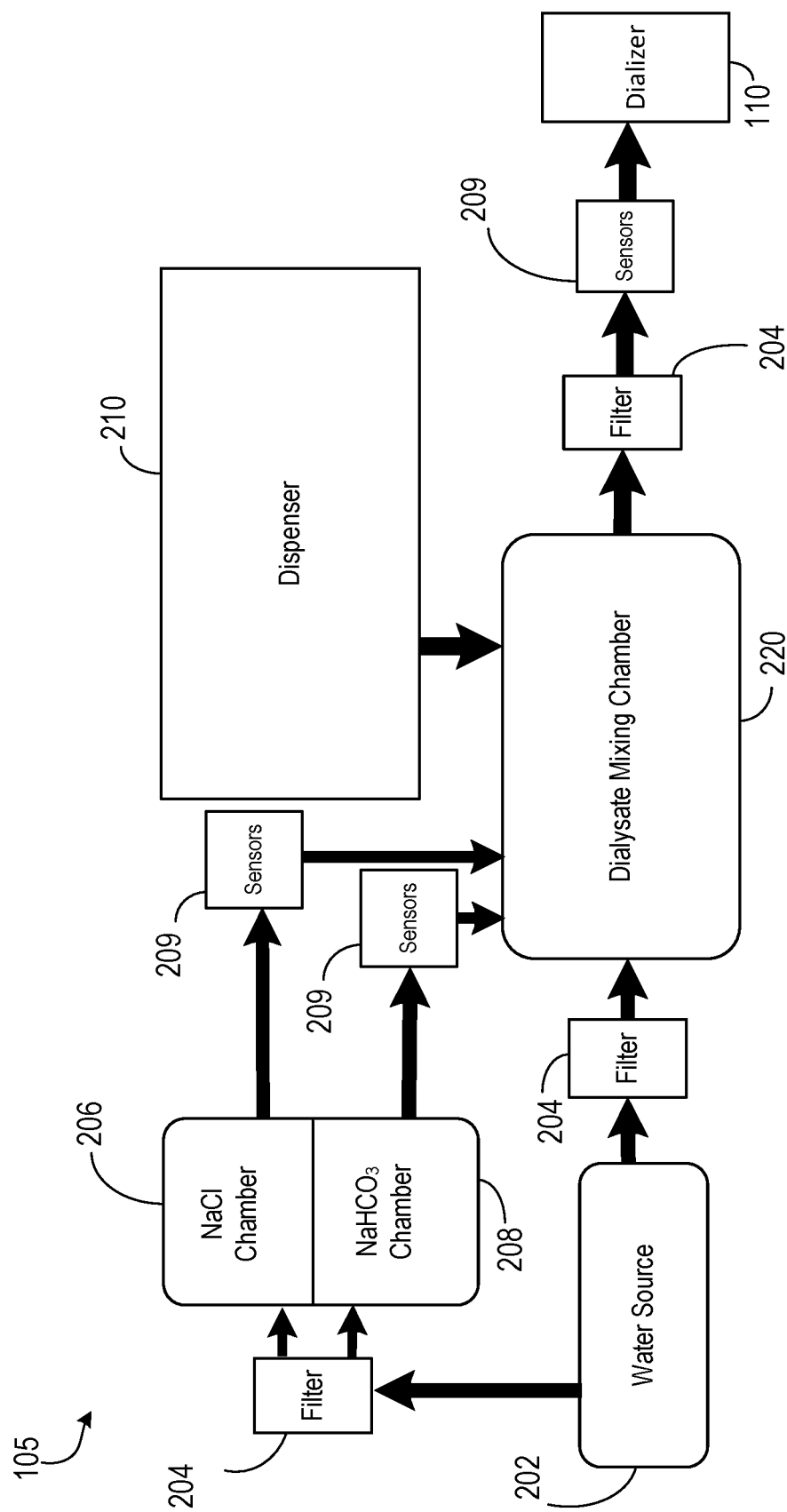
FIG. 2 shows a schematic diagram of the dialysate mixing system of the hemodialysis system of FIG. 1.

FIG. 2 shows a schematic diagram of a dialysate mixing system 105 of the hemodialysis machine 102 of FIG. 1, including the dialysate mixing chamber 220 and components connected thereto. Various components of the hemodialysis machine 102 are not shown in FIG. 1, and are instead described here with respect to their schematic representation.

A water source 202 is connected to the hemodialysis machine 102. In some implementations, the water source 202 is a tap water connection. The water provided by the water source 202 may pass through one or more filters 204 to provide water suitable for use in the dialysis treatment. The water source 202 provides water to a sodium chloride chamber 206 in which the water is mixed with sodium chloride to form a saturated sodium chloride solution. Water is also provided to a bicarbonate chamber 208 in which the water is mixed with bicarbonate to form a saturated bicarbonate solution. The sodium chloride solution and the bicarbonate solution are provided to the dialysate mixing chamber 220 where they are to be mixed with additional components to form the dialysate. In some implementations, the water source 202 is connected to one or more of the sodium chloride chamber 206, the bicarbonate chamber 208, and the dialysate mixing chamber 220 via connections inside the housing 103 of the hemodialysis machine 102.

In some implementations, characteristics of one or both of the sodium chloride solution and the bicarbonate solution can be tested before being provided to the dialysate mixing chamber 220. For example, one or more sensors 209 may be positioned between the sodium chloride chamber 206 and the bicarbonate chamber 208 and the dialysate mixing chamber 220. The sensors 209 may include a temperature sensor and a conductivity sensor for testing the conductivity and the temperature of the sodium chloride solution and the bicarbonate solution. In some implementations, if the temperature and/or the conductivity of either solution is outside of permissible ranges, the solution may be discarded. In some implementations, if the temperature and/or the conductivity of either solution is outside of permissible ranges, the temperature and/or the conductivity can be subsequently tested. For example, one or both of the temperature and the conductivity of the dialysate in the dialysate mixing chamber 220 may be tested by sensors 209 before the dialysate is provided to the dialyzer 110. In this way, sodium chloride solution and/or bicarbonate solution that may initially reside outside of permissible temperature and/or conductivity ranges can still be used in the final dialysate provided the final dialysate resides within permissible temperature and/or conductivity ranges.

The sodium chloride solution and bicarbonate solution are added to the dialysate mixing chamber 220 in appropriate volumes according to the dialysate prescription. The water source 202 provides water (e.g., through a filter 204) to fill the dialysate mixing chamber 220 until the requisite volume of dialysate is achieved.

A dispenser 210 stores a plurality of chemical concentrates to be added to the dialysate mixing chamber 220 to create the dialysate according to the prescription. The chemical concentrates can include one or more of potassium chloride, calcium chloride, magnesium chloride, citric acid, and dextrose, although other chemical concentrates may also be included. After the dispenser 210 dispenses the chemical concentrates in appropriate amounts, the contents of the dialysate mixing chamber 220 are agitated for an appropriate amount of time until the chemical concentrates are sufficiently distributed throughout the dialysate. In some implementations, the contents of the dialysate mixing chamber 220 may be brought to a temperature that facilitates proper mixing of the dialysate. For example, the contents of the dialysate mixing chamber 220 may be heated to approximately body temperature to assist in dissolving and/or distributing the chemical concentrates to yield a homogeneous solution. After the dialysate is prepared, the dialysate is provided to the dialyzer 110 and the rest of the dialysate circuit. The dialysate may undergo one or more final tests before it is provided to the dialyzer 110, such as a conductivity test, a pH test, and/or a temperature test, to ensure that the dialysate has been prepared according to the dialysate prescription and is in proper condition for use in the dialysis treatment.

In some implementations, the chemical concentrates are stored in the dispenser 210 in solid tablet form. For example, each chemical constituent (e.g., potassium chloride, calcium chloride, magnesium chloride, citric acid, dextrose, etc.) may be formed into tablets each having a predetermined weight. The dialysate prescription is processed to determine how many of each tablet is required to make the dialysate. The control unit 101 then causes the dispenser 210 to provide the appropriate number of each tablet. In some implementations, the chemical concentrates are stored in the dispenser 210 in liquid concentrate form, as described in more detail below.

Figure 3:
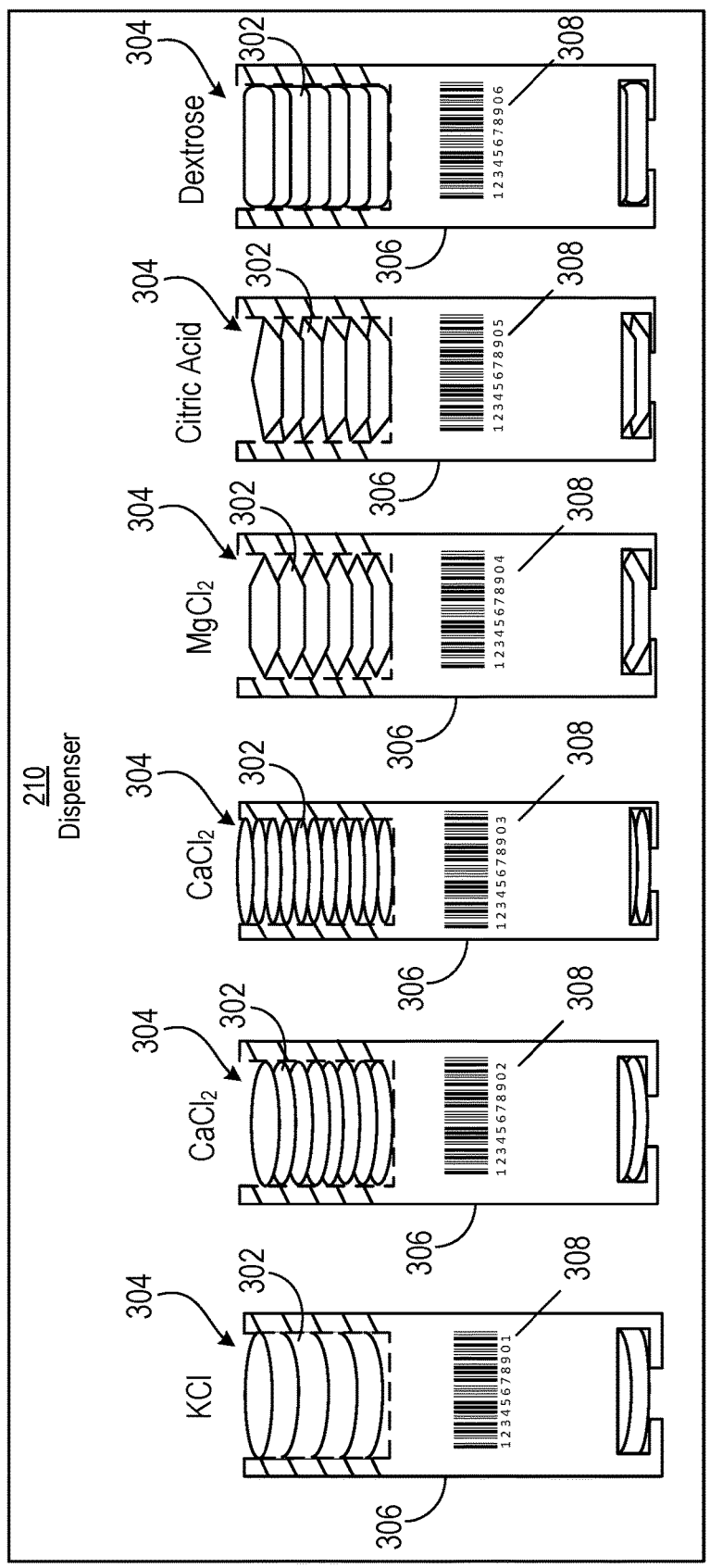
FIG. 3 shows a partial cutaway view of a dispenser of the dialysis mixing system of FIG. 2.

FIG. 3 shows a partial cutaway view of an example of the dispenser 210 of FIG. 2. The dispenser 210 is internal to the housing 103 of the hemodialysis machine 102. In some implementations, each chemical concentrate is stored in the dispenser as a stack 304 of solid tablets 302. Each stack 304 is held in a housing 306 that includes a machine-readable indicium such as a barcode 308 that corresponds to the particular chemical concentrate held in the housing 306. For example, the barcode 308 may include information that identifies the type of chemical concentrate held in the housing 306 and/or an amount of the chemical concentrate in each tablet 302. The dispenser 210 may include a reader that is configured to read data contained in the machine-readable indicium. For example, the dispenser 210 may include a barcode reader that is configured to reach the barcode 308 to automatically determine characteristics of the chemical concentrate upon the stack 304 of tablets 302 being installed into the dispenser 210.

Once the required number of tablets 302 for each chemical concentrate is determined (e.g., according to the prescription, as described below), the control unit 101 of the hemodialysis machine 102 is configured to control one or more dispensing mechanisms that cause the appropriate number of each tablet 302 to be dispensed. For example, each housing 306 that includes a stack 304 of chemical concentrate tablets 302 includes a corresponding dispensing mechanism situated near the bottom of the housing 306. In some implementations, the dispensing mechanism may be an elongated member that resides in a recess behind the lowermost tablet 302 in the stack 304. The control unit 101 may cause the dispensing mechanism to be actuated. For example, the control unit 101 may cause the member to protrude from its corresponding recess and press against the lowermost tablet 302, thereby causing the lowermost tablet 302 to be pushed out of the housing 306 and into the dialysate mixing chamber 220 that resides below the dispenser 210. Once the lowermost tablet 302 has been ejected into the dialysate mixing chamber 220, the member can return to its resting position in the corresponding recess. Upon the member retuning to the recess, the bottom portion of the housing 306 is cleared to allow the stack 304 of tablets 302 to move downwards within the housing 306. If the prescription calls for another one of the particular tablets 302 to be dispensed, the process can be repeated. For example, the member can be actuated again, thereby causing the lowermost tablet 302 to be ejected into the dialysate mixing chamber 220 below. Such a process is repeated for each chemical concentrate until the required number of tablets 302 of each chemical concentrate have been added to the dialysate mixing chamber 220. In some implementations, the dispenser 210 also includes one or more mechanisms to assist the remaining tablets 302 of the stack 304 in moving to the bottom of the housing 306 after a tablet 302 is dispensed.

In some implementations, each stack 304 of tablets 302 may be packaged into the housing 306. When the housing 306 is depleted, the housing 306 can be easily removed and replaced with a new housing 306 including a new stack 304 of tablets 302. In some implementations, when the housing 306 is depleted, the housing 306 may remain in the dispenser 210 and be refilled with a new stack 304 of tablets 302. In some implementations, the stack 304 of tablets 302 may be added to the housing 306 in packaged form (e.g., in a paper roll), and the barcode 308 may be located on the packaging. In some implementations, to avoid any mix ups between different types of tablets, each type of tablet 302 (e.g., potassium chloride, calcium chloride, etc.) may have unique shape and/or the packaging of each type of tablet 302 may bear a unique identifier (e.g., a label and/or a barcode) that matches the unique identifier (e.g., barcode) that may be displayed on the housing 306 (e.g., to assist the user in providing the correct type of tablet 302 to the correct housing 306). In some implementations, the housing 306 may include a barcode reader such that information related to the chemical concentrate is obtained upon the packaged stack 304 of tablets 302 being added to the housing 306 and the barcode 308 being read. In this way, each housing 306 can be associated with a particular chemical concentrate and/or an amount of the particular chemical concentrate. The stacks 304 of tablets 302 can be easily replaced by a patient at his or her home to simplify the dialysate preparation process, while the barcodes 308 and barcode readers ensure that the various chemical concentrates are installed in their appropriate positions and appropriately accounted for by the dispenser 210 to avoid errors in the dispensing and mixing process.

In some implementations, the dispenser 210 may include one or more optical sensor to assist in accurate dispensing of the chemical concentrates. In some implementations, each housing 306 may include an optical sensor that can identify when a tablet 302 is dispensed. For example, if a prescription calls for five of a particular types of tablet 302 to be dispensed, the member can be actuated to cause the lowermost tablet 302 to be ejected into the dialysate mixing chamber 220 below. The optical sensor for the corresponding housing 306 can confirm that the tablet 302 was in fact dispensed. The process can be repeated until five tablets 302 are dispensed (e.g., indicated by five actuations of the member and five instances of the optical sensor confirming that the tablet 302 was ejected). If the member is actuated but the optical sensor does not detect a tablet 302, an error condition may be generated. The error condition may indicate that the particular stack 304 of tablets 302 is empty, thereby requiring replacement and/or refilling.

In some implementations, one or more of the chemical concentrates may have multiple types of tablets 302, with each type including a different amount (e.g., weight) of the chemical concentrate. For example, in the illustrated example, the dispenser 210 includes one stack 304 of calcium chloride tablets 302 in which each tablet 302 includes about 6.62 grams of calcium chloride and another stack 304 of calcium chloride tablets 302 in which each tablet 302 includes about 0.83 grams of calcium chloride. In this way, the necessary denominations of the chemical concentrate are available for adding to the dialysate mixing chamber 220 for making the dialysate according to the prescription.

In some implementations, the tablets 302 for each type of chemical concentrate (and, in some cases, for each amount of a particular chemical concentrate) are visually distinct to minimize the chance of mix ups (e.g., the wrong tablets 302 being added to the wrong housing 306). For example, each type of tablet 302 may have a different color and/or shape. In some implementations, the shape of each housing 306 is such that only tablets 302 having a corresponding shape can be inserted.

The tablets 302 may be manufactured in predetermined weighted amounts based on characteristics of the dialysate to be produced. For example, hemodialysis treatments in the U.S. typically use dialysate with a proportioning ratio of 45x, which includes one-part acid, 1.72 parts base, and 42.28 parts water (in volume). Thus, each 45 liters of dialysate contains 1 liter of acid, 1.72 liters of base, and 42.28 liters of water. A typical dialysis prescription requires 0-4 mEq/L potassium chloride, 0-3 mEq/L calcium chloride, 1 mEq/L magnesium chloride, 2.4 mEq/L citric acid, and either 100 mg/dL dextrose or dextrose-free. The dialysate prescription may call for potassium chloride in 1 mEq/L increments, and the dialysate prescription may call for calcium chloride in 0.25 mEq/L increments. If calcium chloride is required by the prescription, a minimum of 2 mEq/L of calcium chloride is typically required. Therefore, the potassium chloride tablets 302 can be designed such that 1 mEq/L increments of potassium chloride can be achieved in a 45× dialysate of a particular volume (e.g., 45 liters). Similarly, the calcium chloride tablets 302 can be designed such that 2 mEq/L increments of calcium chloride can easily be achieved with a first type of tablet in a 45x dialysate of the particular volume, and 0.25 mEq/L increments of calcium chloride can be achieved with a second type of tablet in a 45x dialysate of the particular volume.

In an example, suppose a prescription calls for 2 mEq/L of potassium chloride and 2.5 mEq/L of calcium chloride. To prepare 45 liters of a 45x dialysate, 6.7 grams of potassium chloride are required and 8.27 grams of calcium chloride are required. Therefore, using this example calculation, each potassium chloride tablet 302 can include 3.35 grams of potassium chloride, each calcium chloride tablet of the first (e.g., larger) type can include 6.62 grams of calcium chloride, and each calcium chloride tablet of the second (e.g., smaller) types can include 0.83 grams of calcium chloride. With tablets 302 of these weights, each potassium chloride tablet 302 provides 1 mEq/L of potassium chloride in 45 liters of 45x dialysate, each calcium chloride tablet of the first (e.g., larger) type provides 2 mEq/L of calcium chloride in 45 liters of 45x dialysate, and each calcium chloride tablet of the second (e.g., smaller) type provides 0.25 mEq/L of calcium chloride in 45 liters of 45x dialysate.

Because the tablets are pre-weighted for use in making 45 liters of 45x dialysate (or, e.g., smaller quantities of dialysate, or, e.g., 35x dialysate, 36.83x dialysate, 36.1 dialysate, etc.) with the appropriate ratio of acid, bicarbonate, and water, their addition to the dialysate will not change their ionic contributions. Therefore, proportioning using acid-base/bicarbonate pumps is not required.

While the example presented above explains a process of mixing 45 liters of 45x dialysate, other (e.g., smaller) quantities of dialysate may be mixed, and dialysate having different proportioning ratios may be mixed. To accommodate such possibilities, the quantities of chemical concentrates in each of the tablets 302 may be modified, and/or additional types of tablets 302 may be provided, such that other types of dialysate can be mixed without requiring an acid-base/bicarbonate proportioning pump systems. Similarly, in some implementations (e.g., when smaller volumes of dialysate are required), the volume of the dialysate mixing chamber 210 may be reduced. Reducing the size of the dialysate mixing chamber 210 can reduce the overall size of the dialysate mixing system 105, thereby increasing the portability of the device. In some implementations, the dialysate mixing chamber 210 may be removable such that a relatively small dialysate mixing chamber can be provided when relatively smaller quantities of dialysate are required, and a relatively larger dialysate mixing chamber can be provided when relatively larger quantities of dialysate are required.

In some implementations, one or more of the chemical concentrates may be included in the dialysate in a fixed amount irrespective of the prescription. For example, the magnesium chloride may be included in the dialysate in an amount of 1 mEq/L, requiring each tablet 302 of magnesium chloride to include 4.58 grams of magnesium chloride to make 45 liters of 45x dialysate. The citric acid may be included in the dialysate in an amount of 2.4 mEq/L, requiring each tablet 302 of citric acid to include 6.91 grams of citric acid. The dextrose may either be omitted from the dialysate or included in the dialysate in an amount of 100 mg/dL, requiring each tablet 302 of dextrose to include 45 grams of dextrose to make 45 liters of 45x dialysate.

Using the dispenser 210 to dispense chemical concentrates in solid tablet 302 form to make a predetermined volume of dialysate as described above, dialysate may be produced according to a particular prescription using eight product codes or fewer. For example, the potassium chloride requires one product code indicating the required number of potassium chloride tablets 302, the calcium chloride requires two product codes indicating the required number of calcium chloride tablets 302 of the first (e.g., larger) type and the required number of calcium chloride tablets 302 of the second (e.g., smaller) type, the magnesium chloride requires one product code indicating the required number of magnesium chloride tablets 302, the citric acid requires one product code indicating the required number of citric acid tablets 302, the dextrose requires one product code indicating the required number of dextrose tablets 302, and each of the sodium chloride and the bicarbonate require one product code each, as described in more detail below. A code (e.g., a concentrate code) can be included in the dialysate prescription, which can be processed by the control unit 101 to determine the number of tablets 302 of each chemical concentrate required to make the dialysate according to the dialysate prescription.

Figure 4:
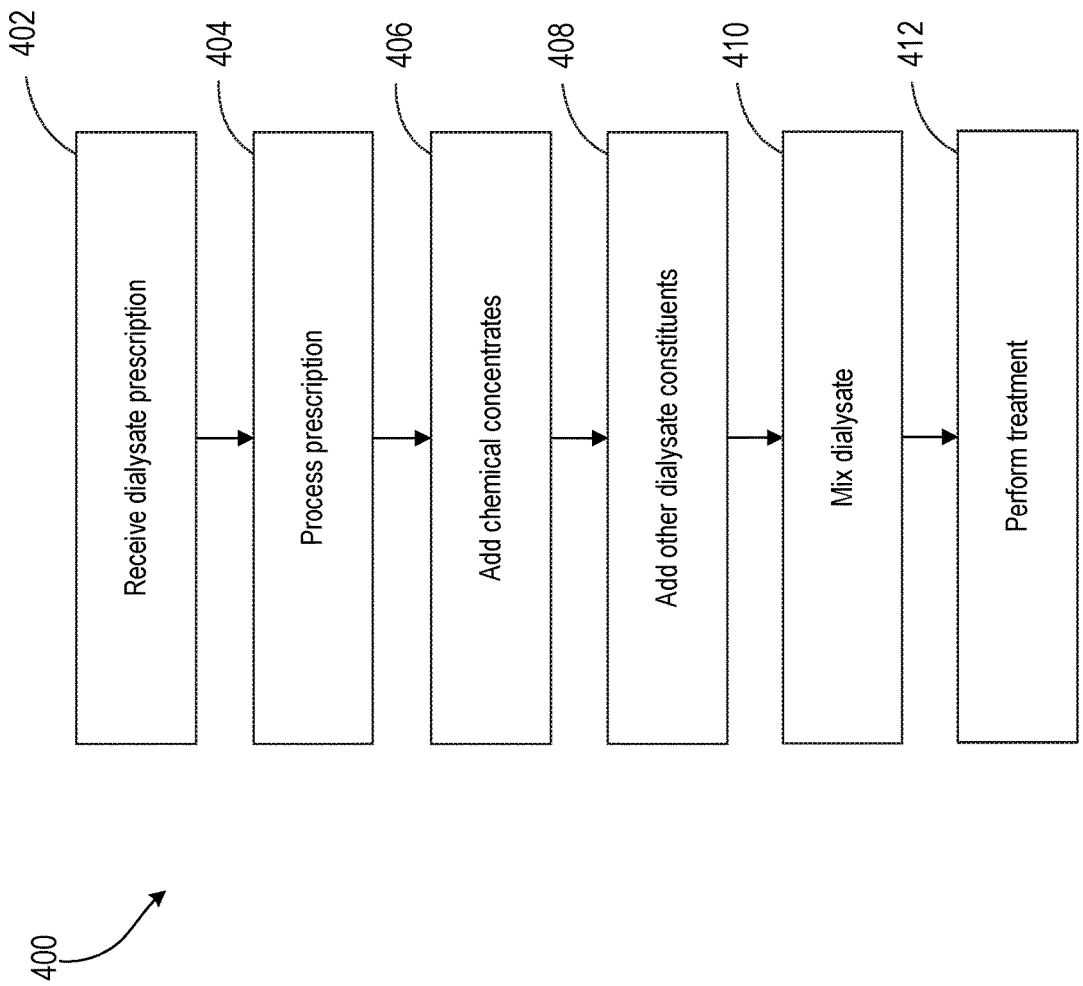
FIG. 4 is a flowchart depicting an example of receiving a dialysate prescription and administering a dialysis treatment.

FIG. 4 is a flowchart 400 depicting an example method of receiving a dialysate prescription and administering a hemodialysis treatment. At step 402, a dialysate prescription is received by the hemodialysis machine 102. The dialysate prescription may be received from a database (e.g., a medical database) over a secured network. In some implementations, receipt of the dialysate prescription requires authentication of one or more persons. For example, in the case of a home hemodialysis treatment, the patient may be required to enter identification information into the hemodialysis machine 102 and/or provide a patient identification card before the dialysate prescription can be accessed. In some cases, a biometric authentication technique may be employed, which may require the patient to provide a finger print and/or other authenticating biometric data. In some implementations, such as for dialysis treatments at a hospital or a clinic, authentication by a medical professional may be required. Once appropriate authentication is obtained, the dialysate prescription can be accessed and the hemodialysis machine 102 can be placed in a ready state.

In some implementations, the hemodialysis machine 102 may be placed in a ready state, and the dialysate preparation may begin, upon patient interaction with the hemodialysis machine 102. For example, the patient may interact with one or both of the touch screen 118 and the control panel 120 of the hemodialysis machine 102 to select a particular dialysate prescription and cause the hemodialysis machine 102 to begin preparing the dialysate. In some implementations, the hemodialysis machine 102 is configured to present a recommended dialysate prescription to be prepared. In some cases, the hemodialysis machine 102 may recommend the previous dialysate prescription that was prepared by the hemodialysis machine 102. Upon patient confirmation, the hemodialysis machine 102 may proceed to prepare dialysate according to the recommended dialysate prescription. In this way, the patient is not required to re-enter excessive information each time the same unchanged dialysate prescription must be prepared, but instead, may cause the dialysate to be prepared with a single confirmatory touch of a button, such as a "Make My Dialysate" button presented on the touch screen 118.

At step 404, the dialysate prescription is processed. For example, the control unit 101 of the hemodialysis machine 102 is configured to read data contained in the dialysate prescription and determine the necessary amounts of each constituent to be included in the dialysate. In an example, the prescription may include, among other things, a concentrate code that indicates the number of tablets 302 of each chemical concentrate to be added to the dialysate mixing chamber 220. In an example, the concentrate code may be "2251-4", where the first digit indicates the concentration of potassium chloride to be included in the dialysate (e.g., 2 mEq/L), the second and third digits indicate the concentration of calcium chloride to be included in the dialysate (e.g., 2.5 mEq/L), and the fourth digit indicates the concentration of magnesium chloride to be included in the dialysate (e.g., 1 mEq/L). The fifth digit may be used for internal use and may have no chemical significance.

The dialysate prescription may also include an indication of the concentration of bicarbonate that is to be provided. The concentration of bicarbonate may be between approximately 20 and 40 mEq/L (e.g., as determined by a nephrologist who assesses the patient acidosis/alkalosis condition). The amount of bicarbonate required to meet the bicarbonate concentration indicated in the prescription may be determined by a characteristic measurement such as an inline conductivity measurement (e.g., by the sensors 209 of FIG. 2). Similarly, the dialysate prescription may also include an indication of the concentration of sodium chloride that is to be provided, and the amount of sodium chloride required to meet the sodium chloride concentration indicated in the prescription may be determined by a characteristic measurement such as an inline conductivity measurement by the sensors 209.

As described above, for a 45-liter batch of 45x dialysate, each tablet 302 of potassium chloride provides 1 mEq/L of potassium chloride for the dialysate. Therefore, the control unit 101 can read the concentrate code and determine that two tablets 302 of potassium chloride are required. Similarly, the control unit 101 can determine that one tablet 302 of calcium chloride of the first (e.g., larger) type is required and two tablets 302 of calcium chloride of the second (e.g., smaller) type are required to achieve 2.5 mEq/L of calcium chloride, and one tablet 302 of magnesium chloride is required to achieve 1 mEq/L of magnesium chloride.

At step 406, the chemical concentrates are added to the dialysate mixing chamber 220. The control unit 101 provides control signals to the dispenser 210 to cause the dispenser 210 to dispense the necessary number of tablets into the dialysate mixing chamber 220. Some of the chemical concentrates are added to the dialysate mixing chamber in fixed amounts irrespective of the dialysate prescription. For example, in some implementations, one tablet 302 of citric acid and one tablet 302 of dextrose may be added to the dialysate mixing chamber 220 to achieve 2.4 mEq/L of citric acid and 100 mg/dL of dextrose, respectively. In some implementations, the dialysate prescription may indicate that the dextrose is to be omitted from the dialysate, in which case dextrose is not added.

At step 408, other dialysate constituents are added to the dialysate mixing chamber 220. As described above with respect to FIG. 2, the dialysate also includes a solution of sodium chloride and a solution of bicarbonate. The dialysate prescription may indicate the concentration of sodium chloride and bicarbonate to be included in the dialysate, and the control unit 101 may cause the sodium chloride solution and the bicarbonate solution to be prepared and provided to the dialysate mixing chamber 220.

With respect to the sodium chloride solution, in some implementations, the concentration of sodium chloride to be included in the dialysate may be fixed (e.g., irrespective of the dialysate prescription). For example, the dialysate may be prepared with a concentration of 100 mEq/L sodium chloride. For 45 liters of 45x dialysate, 263 grams of sodium chloride are required. The 263 grams of sodium chloride can be provided in a cartridge (e.g., a disposable cartridge) and mixed with filtered water in the sodium chloride chamber (206 of FIG. 2) to produce the sodium chloride solution, and the sodium chloride solution can be provided to the dialysate mixing chamber 220 to be mixed with the chemical concentrate tablets 302 and additional filtered water.

With respect to the bicarbonate, the concentration of bicarbonate to be included in the dialysate may be specified in the dialysate prescription. The dialysate prescription may call for bicarbonate having a concentration of 20-40 mEq/L. For 45 liters of 45x dialysate, 139.8 grams of bicarbonate are required (e.g., which corresponds to a pre-mixed bicarbonate concentration of 37 mEq/L, although the bicarbonate concentration may change post-mixing (e.g., to 33 mEq/L) based on neutralizing effects by the particular concentration of acids). The 139.8 grams of bicarbonate can be provided in a cartridge (e.g., a disposable cartridge with bicarbonate in solid or liquid form) and mixed with filtered water in the bicarbonate chamber (208 of FIG. 2) to produce the bicarbonate solution, and the bicarbonate solution can be provided to the dialysate mixing chamber 220 to be mixed with the chemical concentrate tablets 302, the sodium chloride solution, the chemical concentrate tablets 302, and the additional filtered water. In some implementations, a conductivity of the bicarbonate solution and/or the sodium chloride solution can be checked for compliance with the prescription before being added to the dialysate mixing chamber 220 to be combined with the other components of the dialysate.

At step 410, the contents of the dialysate mixing chamber 220 are mixed to form the dialysate according to the dialysate prescription. In some implementations, the contents of the dialysate mixing chamber 220 are agitated for an appropriate amount of time until the chemical concentrates tablets 302 are sufficiently distributed throughout the dialysate and the various constituents are adequately mixed. In some implementations, the contents of the dialysate mixing chamber 220 may be brought to a temperature that facilitates proper mixing of the dialysate. The dialysate may undergo one or more final tests before it is used for the dialysis treatment, such as a conductivity test, a pH test, and/or a temperature test, to ensure that the dialysate has been prepared according to the dialysate prescription and is in proper condition for use in the dialysis treatment.

After the dialysate is prepared, the dialysate is provided to the dialyzer 110 and the rest of the dialysate circuit. At step 412, the dialysis treatment is performed on the patient using the dialysate prepared according to the dialysate prescription.

Using the dialysate preparation technique described herein, dialysate for a particular patient and/or for a particular treatment session can be prepared "on demand" when it is needed. Pre-made dialysate and existing concentrates (e.g., both dry concentrates and liquid concentrates) require large mixing tanks, storage space, and delivery containers (e.g., drums) with known problems and high maintenance costs. If a mistake is made during mixing, or if the dialysate does not meet the requisite prescription, the entire batch of dialysate may be put to waste. Making only the quantity of dialysate required for a particular treatment removes the need for delivering and storing large quantities of dialysate for extended periods of time. Existing concentrates can take on many different forms, requiring an excessive number of product codes to produce a given dialysate. The technique described herein requires only eight product codes, six of which correspond to the chemical concentrates in solid tablet form. The exact proportion of each chemical concentrate can be determined ahead of time for a given quantity of dialysate (e.g., 45x dialysate), and therefore, acid-base proportioning systems are not required in the hemodialysis machine 102, thereby simplifying the operation of the hemodialysis machine 102 and simplifying the process for creating dialysate.

As described above, in some implementations, 45 liters or less of dialysate may be created for a given dialysis treatment. Such a relatively small quantity of dialysate lends itself well to the preparation technique described herein, where minimal dialysate can be created on demand while still maintaining a satisfactory weekly treatment adequacy.

A typical hemodialysis treatment usually requires approximately 120 liters of 45x dialysate. Such a volume is based on a flow fraction of 2:1—e.g., the ratio of dialysate flow (Qd) to blood flow (Qb). When a flow fraction of 2.0 is used, a satisfactory weekly treatment adequacy (e.g., a weekly treatment adequacy above 2.0 Kt/V) can be achieved with a treatment duration of 4 hours, a Qd of 500 mL/min, a Qb of 250-300 mL/min, and three treatments per week.

In some implementations, the flow fraction may be reduced in order to allow adequate treatments to be performed with significantly less dialysate. For example, in some implementations, the flow fraction may be reduced to approximately 0.4. With such a reduced flow fraction, the recommended weekly treatment adequacy of above 2.0 Kt/V can be achieved while requiring as little as 22 liters of dialysate.

While certain implementations have been described, other implementations are possible.

While the various chemical concentrates have been largely described as being provided as tablets in particular quantities, other quantities can also and/or alternatively be used. For example, to assist in mixing and/or dissolving the tablets in the dialysate mixing chamber, one or more of the tablets may be provided in smaller quantities. Provided one or more of the tablets in smaller quantities may also allow higher customizability for the mixed dialysate. In this way, dialysate may be mixed according to relatively higher complexity prescriptions. In some implementations, the chemical concentrates may be provided in tablet sizes such that 0.5 mEq/L increments of potassium chloride, 0.25 mEq/L increments of potassium chloride, 0.1 mEq/L increments of calcium chloride, etc. can be achieved. The dispenser may include additional housings and additional stacks of tablets to accommodate the additional increments for higher customizability of the dialysate prescription.

While the dialysate mixing system has been largely described as being internal to the housing of the dialysis machine, other implementations are possible. For example, in some implementations, one or more of the components of the dialysate mixing system may be located outside of the housing of the dialysis machine and/or may be detachable from the dialysis machine. In some implementations, one or more of the dialysate mixing chamber, the NaCl chamber, the bicarbonate chamber, the dispenser, the water source, and the dialysate mixing chamber may be located outside of the housing of the dialysis machine and/or may be detachable from the dialysis machine. In some implementations, one or more of the components of the dialysate mixing system may be configured to connect to a port on the housing of the dialysis machine and reside substantially outside of the housing of the dialysis machine during use. In this way, the one or more components may be removed and/or disconnected from the dialysis machine when not in use.

While the dialysate mixing system (e.g., the dialysate mixing machine) has largely been described as being incorporated into a dialysis machine, in some implementations, the dialysate mixing machine may be a standalone (e.g., separate) device. For example, in some implementations, the dialysate mixing machine may be a "vending machine" style device that is configured to mix dialysate for immediate or eventual use in a dialysis machine. In some implementations, the components of the dialysate mixing system (105 of FIG. 1) may be included as part of the standalone dialysate mixing machine. For example, the various components of the dialysate mixing system may be included in a single, standalone "vending machine" style device that includes all of the components necessary to mix a dialysate according to a given prescription.

In some implementations, rather than the dialysate mixing chamber being connected to the dialyzer of a dialysis machine via a dialysate supply line, the dialysate mixing chamber may provide the mixed dialysate to a storage vessel for eventual use in a dialysis treatment. For example, after the plurality of chemical concentrates are mixed together in the dialysate mixing chamber, the mixed dialysate may be provided to a storage tank or a storage bottle. The storage tank/bottle may be maintained in the separate dialysate mixing machine until the dialysate is needed for a dialysis treatment. In some implementations, the dialysate mixing machine may maintain the dialysate under proper storage conditions to ensure that the dialysate is in appropriate condition for use in the dialysis treatment when needed. Once the patient is ready to initiate the dialysis treatment (e.g., either immediately after the dialysate is mixed or after a particular period of time), the patient may remove the storage tank/bottle from the separate dialysate mixing machine and provide the storage tank/bottle to the dialysis machine. The dialysis machine may then receive the dialysate from the storage tank/bottle and provide the dialysate to the dialyzer via the dialysate supply line.

In some implementations, the dialysate mixing machine (e.g., when used as a standalone device separate from a dialysis machine) may include one or more components of the dialysis machine described above with respect to FIG. 1. For example, the dialysate mixing machine may include a receiving unit configured to receive a prescription (e.g., from a medical database over a secured network), a control unit (e.g., a processor) configured to process the prescription, a user interface (e.g., a touch screen and/or a control panel) for receiving input for causing the control unit to control the operating parameters of the dialysate mixing machine, etc.

While the dialysis machine has been largely described as being a home dialysis machine for use at the patient's home, in some implementations, the dialysis machine may be located elsewhere. In some implementations, the dialysis machine (e.g., a HD machine or a peritoneal dialysis (PD) machine) may be located at a remote location such as a dialysis clinic or a dialysate filling station. The dialysis machine may receive the dialysate prescription at such remote locations, and dialysate can be made on demand for the patient according to the prescription. In this way, a patient may receive a dialysis treatment according to a prescription specially designed for the patient even when the patient is at remote location (e.g., away from a location at which the patient typically receives dialysis treatments).

In some implementations, the dialysate mixing machine may include a user-friendly user interface to assist the user (e.g., the patient) in easily mixing dialysate according to an appropriate prescription. For example, the user interface may include a display screen (e.g., a touch screen), a "start" button or a "make my dialysate" button, and a "stop" button. For example, when used as a standalone device separate from the dialysis machine, the dialysate mixing machine may begin mixing dialysate according to the patient's prescription with just a few button presses. The patient (e.g., after being verified and/or entering patient identification information) may select an appropriate prescription using the touch screen. In some implementations, if the patient has already mixed dialysate according to a particular prescription, that particular prescription may be automatically selected by default. Thus, the patient may initiate mixing of another batch of dialysate according to that particular prescription by simply interacting with the "start" or "make my dialysate" button. If any issues (e.g., error condition) arise during mixing of the dialysate, the patient can interact with the "stop" button to cause the mixing process to cease.

While the systems and techniques for creating dialysate have been largely described herein with respect to a hemodialysis system (e.g., an HD machine for use at a patient's home), other medical treatment systems can employ the techniques described herein. Examples of other medical treatment systems include PD systems, hemofiltration systems, and hemodiafiltration systems, among others.

In some implementations, the dialysis machine is a PD machine that is configured to make PD solution according to a PD prescription and administer a PD treatment to the patient.

Figure 5:
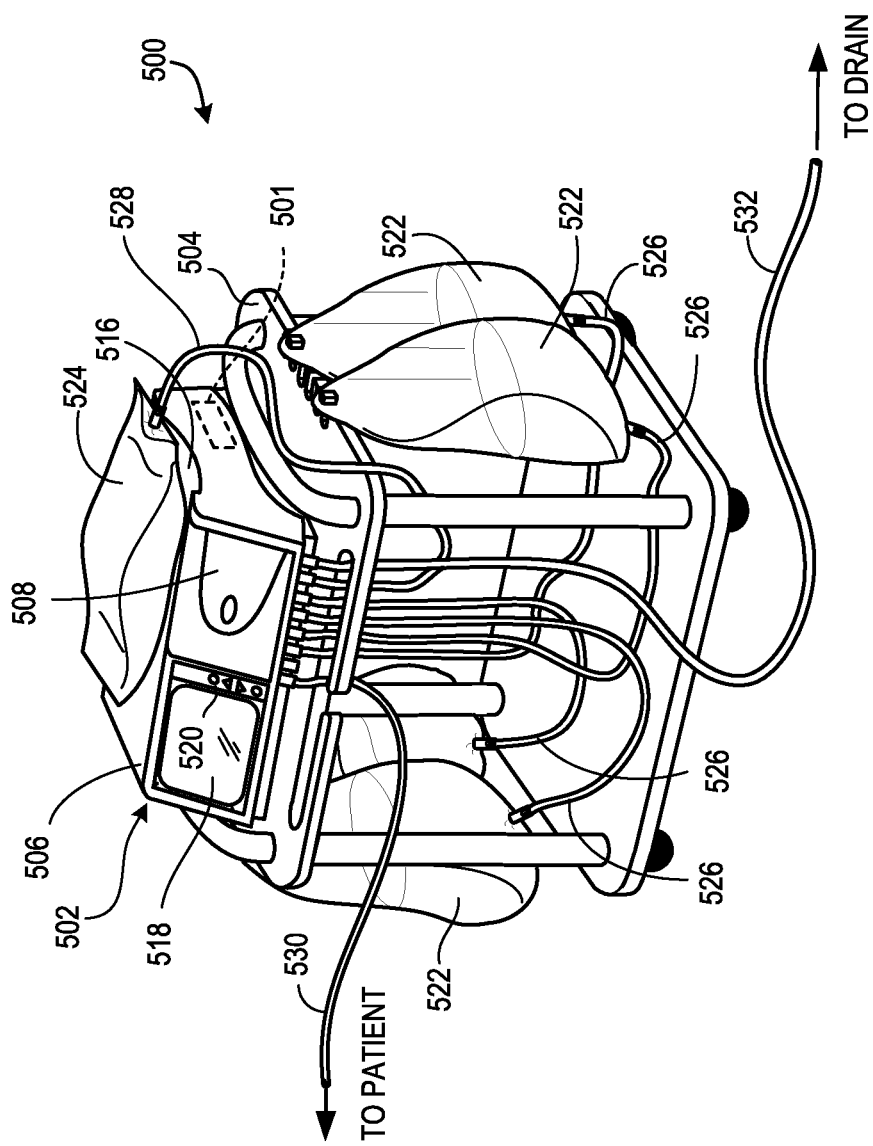
FIG. 5 shows a front perspective view of a peritoneal dialysis (PD) system that includes a PD mixing system.

FIG. 5 shows an example of a PD system 500 that is configured to make PD solution according to a PD prescription. In some implementations, the PD system 500 is configured for use at a patient's home (e.g., a home PD system). The PD system 500 includes a PD machine (also referred to as a PD cycler) 502 seated on a cart 504. The PD machine 502 includes a housing 506, a door 508, and a cassette interface that contacts a disposable PD cassette when the cassette is disposed within a cassette compartment formed between the cassette interface and the closed door 508. A heater tray 516 is positioned on top of the housing 506. The heater tray 516 is sized and shaped to accommodate a heater bag 524. The heater tray 516 is configured to heat dialysate contained in the heater bag 524 to the appropriate temperature before being introduced into the patient's body. The PD machine 502 also includes a user interface such as a touch screen 518 and control panel 520 that can be operated by a user (e.g., a caregiver or a patient) to allow, for example, set up, initiation, and/or termination of a PD treatment.

Dialysate bags 522 are suspended from fingers on the sides of the cart 504, and the heater bag 524 is positioned in the heater tray 516. The dialysate bags 522 and the heater bag 524 are connected to the cassette via dialysate bag lines 526 and a heater bag line 528, respectively. The dialysate bag lines 526 can be used to pass dialysate from dialysate bags 522 to the cassette during use, and the heater bag line 528 can be used to pass dialysate back and forth between the cassette and the heater bag 524 during use.

The PD system 500 includes a PD mixing system similar to the dialysate mixing system 105 described above with respect to FIGS. 1-3. In particular, the PD mixing system includes a water source, a sodium chloride mixing chamber, a bicarbonate mixing chamber, a dispenser, and a PD mixing chamber. The dispenser is configured to dispense chemical concentrates (e.g., in solid tablet form and/or liquid concentrate form) into the PD mixing chamber to be mixed with water, sodium chloride solution, and bicarbonate solution to form a PD solution according to a PD prescription. The PD solution can be provided to the dialysate bags 522 for storage before being provided to the cassette and/or the heater bag 524 in the manner described above. The components of the PD mixing system are largely internal to the housing 506 of the PD machine 502.

A patient line 530 and a drain line 532 are connected to the cassette. The patient line 530 can be connected to a patient's abdomen via a catheter and can be used to pass dialysate back and forth between the cassette and the patient's peritoneal cavity during use. The drain line 532 can be connected to a drain or drain receptacle and can be used to pass dialysate from the cassette to the drain or drain receptacle during use.

The touch screen 518 and the control panel 520 allow an operator to input various treatment parameters to the PD machine 502 and to otherwise control the PD machine 502. In addition, the touch screen 518 servers as a display. The touch screen 518 functions to provide information to the patient and the operator of the PD system 500. For example, the touch screen 518 may display information related to a dialysis treatment to be applied to the patient, including information related to a prescription.

In some implementations, a PD prescription for a particular patient may be received by the PD machine 502 from a medical database over a secured network. After the patient is authenticated, the PD machine 502 may be placed in a ready state. The patient may interact with one or both of the touch screen 518 and the control panel 520 to cause the PD treatment to initiate. The patient can select the appropriate PD prescription, and the PD machine 502 may prepare the PD solution accordingly. In some implementations, the PD machine 502 may automatically recommend that a PD solution be prepared according to the PD prescription most recently used by the PD machine 502. In this way, the patient is not required to re-enter excessive information each time the same unchanged PD prescription must be prepared, but instead, may cause the PD solution to be prepared with a single confirmatory touch of a button, such as a "Make My PD solution" button presented on the touch screen 518.

The PD machine 502 includes a control unit 501 that resides inside the PD machine 502 and which is configured to communicate with the touch screen 518 and the control panel 520. The control unit 501 is configured to receive data from the touch screen 518 and the control panel 520 and control the PD machine 502 based on the received data. For example, the control unit 501 can adjust the operating parameters of the PD machine 502. In some implementations, the control unit 501 is an MPC823 PowerPC device manufactured by Motorola, Inc.

In some implementations, the particular characteristics of the dialysate prescription described above may be modified to make a PD solution appropriate for use in a PD treatment. The PD solution may include one or more additional chemical constituents and/or may omit one or more of the chemical constituents described above with respect to the HD dialysate. Additionally, in some implementations, the water used in connection with the PD solution may be appropriately purified via a water purification system to a level sufficient for use in a PD treatment.

While the machine-readable indicium included on the housing and/or packaging of each stack of solid tablets has largely been described as a barcode that is configured to interact with a barcode reader, other machine-readable indicium may also or alternatively be used. In some implementations, the housing may include an NFC tag (e.g., an RFID tag) that includes information that identifies the type of chemical concentrate held in the housing and/or an amount of the chemical concentrate in each tablet. Likewise, the dispenser may include an NFC reader (e.g., an RFID reader) that is configured to read the information contained in the corresponding tag. In some implementations, other short-range communication protocols may be used to allow the housing and/or packaging to automatically transfer information related to the chemical concentrate included therein to the control unit, such as a Bluetooth protocol.

While the dispenser has been largely described as being configured to provide chemical concentrates in solid tablet form, other forms are also possible. For example, in some implementations, one or more of the chemical concentrates may be provided in a liquid form, and the dispenser may be configured to provide the chemical concentrates in liquid form in amounts to achieve dialysate according to the dialysate prescription.

In some implementations, rather than the dispenser being configured to dispense the solid tablets of chemical concentrate, the dispenser may be configured to manage the dispensing of chemical concentrates in liquid form. For example, each chemical concentrate may be provided in a vial (e.g., a disposable vial) that includes the chemical concentrate and a liquid (e.g., a saline solution). Each vial that includes the liquid chemical concentrate may be configured to fit into a corresponding chamber in the dispenser. Each chamber of the dispenser may include a pump, a fluid line, and a valve that is in fluid communication with the corresponding vial. When the pump is actuated and the valve is opened, the liquid chemical concentrate may be dispensed into the dialysate mixing chamber.

For example, the control unit of the dialysis machine may be configured to read the dialysate prescription and determine the amount of each liquid chemical concentrate that is needed to create the dialysate. For each chemical concentrate, the control unit may be configured to open the valve and operate the pump for a particular amount of time depending on the amount of the particular chemical concentrate required. In some implementations, one or more volumetric flow sensors may be used to determine the volume of liquid chemical concentrate added to the dialysate mixing chamber. In this way, the control unit may communicate with the volumetric flow sensors and cause each liquid chemical concentrate to be added to the dialysate mixing chamber until the volumetric flow sensors indicate that the requisite volume of each liquid chemical concentrate has been added. When a liquid chemical concentrate is finished being added (or, e.g., the particular chemical concentrate is not required for the given prescription), the corresponding valve of the fluid line may be closed.

In some implementations, one or more of the chemical concentrates can be dissolved in a concentrated solution that is stored in the dispenser of the dialysis machine. After the prescription is received and processed by the control unit of the dialysis machine, the control unit can determine the appropriate amount of each liquid chemical concentrate required to produce a given volume of dialysate having the appropriate characteristics according to the prescription. For example, a concentrate code of "2251-4" may be included in the prescription, indicating that a concentration of 2 mEq/L of potassium chloride is required, a concentration of 2.5 mEq/L of calcium chloride is required, and a concentration of 1 mEq/L of magnesium chloride is required. To make a given volume of dialysate (e.g., 45 liters), the liquid chemical concentrates may be pre-weighted such that, for example, 1 cc of the potassium chloride solution corresponds to 1 mEq/L concentration of potassium chloride in the final dialysate, 0.25 cc of the calcium chloride solution corresponds to 0.25 mEq/L concentration of calcium chloride in the final dialysate, and 1 cc of the magnesium chloride solution corresponds to 1 mEq/L concentration of magnesium chloride in the final dialysate. Therefore, each of the liquid chemical concentrates can be added in their requisite amount to the dialysate mixing chamber in order to achieve a dialysate having the characteristics defined by the dialysate prescription using principles similar to those described above with respect to the solid tablet chemical concentrates.

Figure 6:
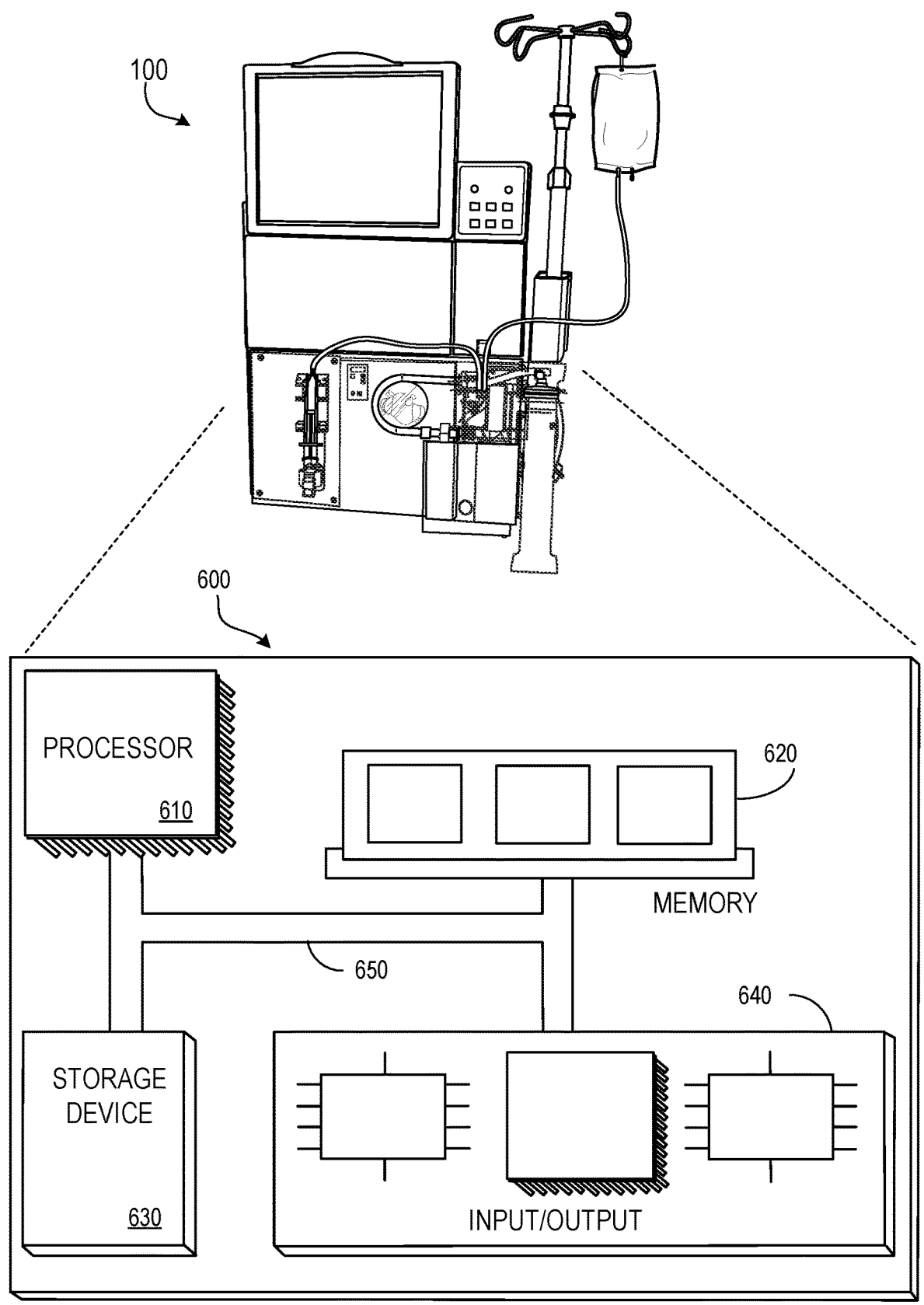
FIG. 6 shows an example of a computer system of the hemodialysis system of FIG. 1 or the PD system of FIG. 5.

FIG. 6 is a block diagram of an example computer system 600. For example, referring to FIGS. 1 and 5, the control unit 101, 501 could be an example of the system 600 described here. The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the dialysis system create dialysate according to the processed dialysate prescription.

The memory 620 stores information within the system 600. In some implementations, the memory 620 is a computer-readable medium. The memory 620 can, for example, be a volatile memory unit or a non-volatile memory unit.

The storage device 630 is capable of providing mass storage for the system 600. In some implementations, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some implementations, the information stored on the memory 620 can also or instead be stored on the storage device 630.

The input/output device 640 provides input/output operations for the system 600. In some implementations, the input/output device 640 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 640 includes driver devices configured to receive input data and send output data to other input/output devices, e.g., a keyboard, a printer, and display devices (such as the touch screen display 118 or 518). In some implementations, the input/output device 640 receives the dialysate prescription (e.g., wirelessly) for processing by the dialysis machine. In some implementations, mobile computing devices, mobile communication devices, and other devices are used.

In some implementations, the system 600 is a microcontroller. A microcontroller is a device that contains multiple elements of a computer system in a single electronics package. For example, the single electronics package could contain the processor 610, the memory 620, the storage device 630, and input/output devices 640.

Although an example processing system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them.

Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, a composition of matter effecting a machine-readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A dialysate mixing machine comprising:
a dialysate mixing chamber;
a dispenser configured to provide chemical concentrates in solid tablet form to create a dialysate;
one or more sensors configured to provide measurements to a processor; and
the processor configured to:
process a dialysate prescription to cause the dispenser to provide the chemical concentrates in amounts based on the dialysate prescription, wherein the dialysate prescription includes information indicating particular chemical constituents and amounts of each of the chemical constituents to be included in the dialysate, and wherein the chemical concentrates are combined with at least water to form a plurality of solutions according to the dialysate prescription;
obtain, from the one or more sensors, a plurality of conductivity measurements, wherein each of the plurality of conductivity measurements indicates a conductivity measurement for an individual solution of the plurality of solutions, and wherein each of the plurality of conductivity measurements is associated with one of the chemical constituents;
determine that a first conductivity measurement of the plurality of conductivity measurements associated with a first solution of the plurality of solutions is outside of a permissible range identified by the dialysate prescription;
based on determining that the first conductivity measurement is outside of the permissible range, discard the first solution;
re-make the first solution by causing the dispenser to provide a first chemical constituent, of the chemical constituents, associated with the first solution; and
create the dialysate in the dialysate mixing chamber using the re-made first solution and at least one solution of the plurality of solutions other than the discarded first solution.

2. The dialysate mixing machine of claim 1, wherein a size and shape of the solid tablets for each chemical concentrate is different than a size and shape of the solid tablets for each other chemical concentrate.

3. The dialysate mixing machine of claim 1, wherein the dialysate prescription indicates a number of solid tablets to be dispensed for each chemical concentrate.

4. The dialysate mixing machine of claim 1, wherein each chemical concentrate is stored in the dispenser as a stack of solid tablets.

5. The dialysate mixing machine of claim 4, wherein each stack of solid tablets is held in a housing that includes a machine-readable indicium, wherein the machine-readable indicium includes information related to the chemical concentrate held in the housing.

6. The dialysate mixing machine of claim 5, wherein the machine-readable indicium is a barcode.

7. The dialysate mixing machine of claim 6, wherein the barcode includes information related to a type of the chemical concentrate and an amount of the chemical concentrate in each tablet.

8. The dialysate mixing machine of claim 1, wherein the chemical concentrates comprise one or more of potassium chloride, calcium chloride, magnesium chloride, citric acid, and dextrose.

9. The dialysate mixing machine of claim 1, wherein the dialysate prescription indicates that the dialysate is to have a proportioning ratio of 45X.

10. The dialysate mixing machine of claim 1, wherein the plurality of solutions comprises a bicarbonate solution, wherein the bicarbonate solution is combined in the dialysate mixing chamber to create the dialysate.

11. The dialysate mixing machine of claim 10, wherein the plurality of solutions further comprises a sodium chloride solution, wherein the sodium chloride solution is also combined in the dialysate mixing chamber to create the dialysate.

12. The dialysate mixing machine of claim 11, wherein the one or more sensors are one or more conductivity sensors, wherein the plurality of conductivity measurements comprise conductivity measurements of the bicarbonate solution and the sodium chloride solution.

13. The dialysate mixing machine of claim 1, further comprising a receiver configured to receive the dialysate prescription.

14. The dialysate mixing machine of claim 13, wherein the receiver is configured to receive the dialysate prescription wirelessly from a medical database.

15. A dialysis system comprising:
a dialysis machine; and
a dialysate mixing machine coupled to the dialysis machine and comprising:
  a dialysate mixing chamber;
  a dispenser configured to provide chemical concentrates in solid tablet form to create a dialysate;
  one or more sensors configured to provide measurements to a processor; and
  the processor configured to:
    process a dialysate prescription to cause the dispenser to provide the chemical concentrates in amounts based on the dialysate prescription, wherein the dialysate prescription includes information indicating particular chemical constituents and amounts of each of the chemical constituents to be included in the dialysate, and wherein the chemical concentrates are combined with at least water to form a plurality of solutions according to the dialysate prescription;
    obtain, from the one or more sensors, a plurality of conductivity measurements, wherein each of the plurality of conductivity measurements indicates a conductivity measurement for an individual solution of the plurality of solutions, and wherein each of the plurality of conductivity measurements is associated with one of the chemical constituents;
    determine that a first conductivity measurement of the plurality of conductivity measurements associated with a first solution of the plurality of solutions is outside of a permissible range identified by the dialysate prescription;
    create the dialysate in the dialysate mixing chamber using the plurality of solutions;
    based on the determination that the first conductivity measurement associated with the first solution is outside of the permissible range, obtain, from the one or more sensors, a second conductivity measurement of the created dialysate;
    compare the second conductivity measurement with the information from the dialysate prescription;
    based on comparing the second conductivity measurement with the information from the dialysate prescription, re-create the dialysate in the dialysate mixing chamber; and
    provide the re-created dialysate to the dialysis machine.

16. The dialysis system of claim 15, wherein the dialysis machine is a hemodialysis machine comprising:
a blood pump configured to pump blood to and from a patient; and
a dialyzer configured to receive the blood from the patient and the dialysate from the dialysate mixing chamber, remove toxins from the blood, and provide filtered blood to the patient.

17. The dialysate system of claim 16, wherein the blood and the dialysate flow through the dialyzer at a flow fraction of less than 0.5.

18. The dialysate system of claim 17, wherein 45 liters or less of dialysate are made in the dialysate mixing chamber, and the hemodialysis machine provides a hemodialysis treatment to the patient using the 45 liters or less of dialysate.

19. A method comprising:
receiving, by a hemodialysis machine, a dialysate prescription; and
causing a dispenser of the hemodialysis machine to provide chemical concentrates in solid tablet form to a dialysate mixing chamber in amounts based on the dialysate prescription, wherein the dialysate prescription includes information indicating particular chemical constituents and amounts of each of the chemical constituents to be included in a dialysate, and wherein the chemical concentrates are combined with at least water to form a plurality of solutions according to the dialysate prescription;
obtaining, from one or more sensors of the hemodialysis machine, a plurality of conductivity measurements, wherein each of the plurality of conductivity measurements indicates a conductivity measurement for an individual solution of the plurality of solutions, and wherein each of the plurality of conductivity measurements is associated with one of the chemical constituents;
determining that a conductivity measurement of the plurality of conductivity measurements associated with the first solution is outside of a permissible range identified by the dialysate prescription;
based on determining that the first conductivity measurement is outside of the permissible range, discarding the first solution;
re-making the first solution by causing the dispenser to provide a chemical constituent, of the chemical constituents, associated with the first solution; and
creating the dialysate in the dialysate mixing chamber using the re-made first solution and at least one solution of the plurality of solutions other than the discarded first solution.

20. The method of claim 19, wherein the dialysate prescription indicates a number of solid tablets to be dispensed for each chemical concentrate.

21. The method of claim 19, wherein each chemical concentrate is stored in the dispenser as a stack of solid tablets.

22. The method of claim 21, wherein each stack of solid tablets is held in a housing that includes a machine-readable indicium, wherein the machine-readable indicium includes information related to the chemical concentrate held in the housing.

23. The dialysis system of claim 15, further comprising:
a medical database, wherein the medical database is configured to provide the dialysate prescription to the dialysate mixing machine via a secured network.

24. The dialysate mixing machine of claim 1, wherein the processor is further configured to:
provide the created dialysate to a peritoneal dialysis machine.

25. The dialysis system of claim 15, wherein the dialysis machine is a peritoneal dialysis machine.

* * * * *